(12) United States Patent
Heggadahalli

(10) Patent No.: US 11,911,307 B2
(45) Date of Patent: Feb. 27, 2024

(54) KNEE BRACE

(71) Applicant: Bharath Heggadahalli, Southborough, MA (US)

(72) Inventor: Bharath Heggadahalli, Southborough, MA (US)

(*) Notice: Subject to any disclaimer, the term of this patent is extended or adjusted under 35 U.S.C. 154(b) by 510 days.

(21) Appl. No.: 16/862,769

(22) Filed: Apr. 30, 2020

(65) Prior Publication Data
US 2021/0228392 A1 Jul. 29, 2021

Related U.S. Application Data

(60) Provisional application No. 62/965,087, filed on Jan. 23, 2020.

(51) Int. Cl.
*A61F 5/01* (2006.01)

(52) U.S. Cl.
CPC .... *A61F 5/0123* (2013.01); *A61F 2005/0155* (2013.01); *A61F 2005/0188* (2013.01)

(58) Field of Classification Search
CPC .... A61F 5/0106; A61F 5/0109; A61F 5/0123; A61F 2005/0155; A61F 2005/0188
See application file for complete search history.

(56) References Cited

U.S. PATENT DOCUMENTS

| | | | | |
|---|---|---|---|---|
| 10,076,462 | B2* | 9/2018 | Johnson | A41D 1/005 |
| 2016/0317084 | A1* | 11/2016 | DeLuke | A61F 5/3738 |
| 2021/0196500 | A1* | 7/2021 | Gu | A61F 5/0123 |

OTHER PUBLICATIONS

Bodor, "Quadriceps protects the anterior cruciate ligament," J. Orthop. Res., Jul. 2001, 19(4):629-633, 5 pages.
Bogardus et al., "Applying the socio-ecological model to barriers to implementation of ACL injury prevention programs: A systematic review," J. Sport Health Sci., Nov. 2017, 8(1):8-16, 9 pages.
Dai et al., "Anterior cruciate ligament injuries in soccer: Loading mechanisms, risk factors, and prevention programs," J. Sport Health Sci., Jul. 2014, 3(4):299-306, 8 pages.
DJOGlobal.com [online], "A22™ Custom Knee Brace", upon information and belief, available no later than Jun. 3, 2018, retrieved Mar. 28, 2022, retrieved from URL <https://www.djoglobal.com/products/donjoy/a22-custom-knee-brace?landingpage=false>, 2 pages.

(Continued)

*Primary Examiner* — Keri J Nelson
(74) *Attorney, Agent, or Firm* — Fish & Richardson P.C.

(57) ABSTRACT

A knee brace includes a flexible sleeve made of a flexible fabric; a memory device configured to store a reference configuration of the flexible sleeve; a first sensor configured to detect a configuration of the flexible sleeve; and a sleeve tightening mechanism configured to adjust a tightness of the flexible sleeve. A controller is configured to receive an output signal representing, or indicative of, the detected configuration from the first sensor, compare the detected configuration with the reference configuration, and control the sleeve tightening mechanism based on a result of a comparison of the detected configuration of the flexible sleeve and the reference configuration of the flexible sleeve.

33 Claims, 15 Drawing Sheets

(56) References Cited

OTHER PUBLICATIONS

DJOGlobal.com [online], "Defiance Custom Knee Brace", available on or before Aug. 1, 2017, via internet archive: Wayback Machine URL <https://web.archive.org/web/20170801041222/https://www.djoglobal.com/our-brands/donjoy/defiance>, retrieved on Mar. 28, 2022, URL <https://www.djoglobal.com/our-brands/donjoy/defiance>, 14 pages.

DJOGlobal.com [online], "Donjoy Defiance," upon information and belief, available no later than Jan. 4, 2018, retrieved Mar. 24, 2022 from URL <https://www.djoglobal.com/products/donjoy/defiance?landingpage=false>, 1 page.

Donjoyperformance.com [online], "Bionic Fullstop Knee Brace" upon information and belief, available No. later than Mar. 8, 2016, retrieved Mar. 28, 2022, retrieved from URL <https://www.donjoyperformance.com/bionic-fullstop-knee-brace>, 10 pages.

Grood et al., "Letter to the editor," J. Orthop. Res., Sep. 2002, 20(5):1129-30, 2 pages.

Jalali et al., "The effect of functional bracing on the arthrokinematics of anterior cruciate ligament injured knees during lunge exercise," Gait & Posture, Jun. 2018, 63:52-57, 6 pages.

matrixortho.com [online], "Post-Op Program", available on or before Dec. 2, 2020, retrieved Mar. 28, 2022, retrieved from URL <https://www.matrixortho.com/post-op-program>, 3 pages.

Mok et al. "Measurement of movement patterns to enhance ACL injury prevention—A dead end?," Asia Pac. J. Sports Med. Arthrosc. Rehabil. Technol., Jul. 2016, 5:13-16, 4 pages.

Moon et al., "Effect of wearing a knee brace or sleeve on the knee joint and anterior cruciate ligament force during drop jumps: A clinical intervention study," The Knee, Dec. 2018, 25(6):1006-1015, 7 pages.

Murray et al., "Biology of Anterior Cruciate Ligament Injury and Repair: Kappa Delta Ann Doner Vaughn Award Paper 2013," J. Orthop. Res., Jul. 2013, 31(10):1501-1506, 6 pages.

Neville et al., "Validation of method for analysing mechanics of unloader brace for medial knee osteoarthritis," J. Biomech., Jul. 2018, 76:253-258, 6 pages.

Silvers et al., "ACL Injury Prevention in the Athlete," Sport-Orthopädie—Sport-Traumatologie, 2011, 27(1):18-26, 9 pages.

The Anterior Cruciate Ligament: Reconstruction and Basic Science 2nd ed., Prodromos (ed)., Jul. 2017, Chapter 5, 12 pages.

Wordpress [online], "X4 Smart Brace with Motion Intelligence Technology," upon information and belief, available no later than Jun. 1, 2020, retrieved on Mar. 28, 2022, retrieved from URL <https://tsbbracing.files.wordpress.com/2020/06/donjoy-x4-smart-brace.pdf>, 2 pages.

\* cited by examiner

KNEE BRACE

CROSS-REFERENCE TO RELATED APPLICATION

This application claims priority to U.S. provisional patent application 62/965,087, filed on Jan. 23, 2020. The entire contents of the above application are hereby incorporated by reference.

TECHNICAL FIELD

This disclosure relates to knee braces.

BACKGROUND

One type of severe injury that occurs in sports is an anterior cruciate ligament (ACL) tear. In the U.S., many people suffer from anterior cruciate ligament injuries every year. These tears take a long time to heal and generate an increased risk of knee osteoarthritis, a condition in which the cartilage in the knee wears away. Some braces prevent the extension of the anterior cruciate ligament, but they also limit the range of motion, de-incentivizing the use of such braces by athletes. Some braces allow the fluidity of motion that athletes require but do not provide enough support to prevent anterior cruciate ligament tears.

SUMMARY

This specification describes a knee brace that may reduce the rate of anterior cruciate ligament tears. In some implementations, the knee brace uses data from an electronic goniometer, a device that measures angles, to determine an angle of knee bending, and selectively apply pressure on the knee when an excess knee bending is detected. For example, when the electronic goniometer detects the knee bending beyond a threshold angle, pressure is applied to the knee to reduce further bending. If the knee angle is below the threshold angle, the brace is configured to allow the knee to have a free range of motion. This way, the anterior cruciate ligament can have additional support when needed without unduly restricting the movements of the user. For example, by using the knee brace described in this specification, the maximum angle of the knee during a sudden movement can be lower than that allowed by other conventional braces. The knee brace reduces the time that the anterior cruciate ligament is in a vulnerable position, thereby reducing the chance of an anterior cruciate ligament injury.

In one aspect, the disclosure features an apparatus comprising a knee brace that includes: a flexible sleeve that includes a flexible fabric; a memory device configured to store a reference configuration of the flexible sleeve; a first sensor configured to detect a configuration of the flexible sleeve; a sleeve tightening mechanism configured to adjust a tightness of the flexible sleeve; and a controller configured to receive an output signal representing, or indicative of, the detected configuration from the first sensor, compare the detected configuration with the reference configuration, and control the sleeve tightening mechanism based on a result of a comparison of the detected configuration of the flexible sleeve and the reference configuration of the flexible sleeve.

In another aspect, a method of providing support to a knee of a user includes: wearing a flexible sleeve around the knee, in which the flexible sleeve includes a flexible fabric; detecting, using a first sensor, a bending of the flexible sleeve; and adjusting a tightness of the flexible sleeve around the knee based on an output signal of the first sensor.

Implementations of the aspects above can include one or more of the following features. Adjusting a tightness of the flexible sleeve can include using a controller to control a sleeve tightness adjustment mechanism to adjust a tightness of the flexible sleeve. The first sensor can be configured to measure an angle of bending of the flexible sleeve, and the reference configuration of the flexible sleeve can include a reference angle of bending of the flexible sleeve.

The controller can be configured to compare the measured angle of bending of the flexible sleeve with the reference angle of bending of the flexible sleeve, and control the sleeve tightening mechanism based on a result of a comparison of the measured angle of bending of the flexible sleeve and the reference angle of bending of the flexible sleeve.

The controller can be configured to control the sleeve tightening mechanism to tighten the flexible sleeve, as compared to a normal state of the flexible sleeve, if the result of the comparison of the measured angle and the reference angle meets a first criterion.

The controller can be configured to control the sleeve tightening mechanism to tighten the flexible sleeve, as compared to the normal state of the flexible sleeve, if the measured angle is greater than the reference angle by a predetermined threshold.

The flexible sleeve can be configured to be worn on a user's knee, and the controller can be configured to control the sleeve tightening mechanism to tighten the flexible sleeve, as compared to the normal state of the flexible sleeve, if the result of the comparison of the measured angle and the reference angle indicates that a bending of the knee meets a predetermined criterion.

In some examples, the predetermined criterion can include an angle between a backside of the user's small leg immediately below the knee and a backside of the user's thigh immediately above the knee being greater than 180°, or 185°, or 190°.

The controller can be configured to perform a calibration procedure to determine the reference configuration, and store the reference configuration in the memory device.

The controller can be configured to perform the calibration procedure to determine a reference angle of bending of the flexible sleeve when the knee brace is worn by a user in a reference position.

The reference position can include the user's leg extending straight or in a full knee extension.

The first sensor can include a flex sensor that is configured to have a resistance that varies in accordance to the angle of bending of the flexible sleeve, and the flex sensor can be configured to generate an output signal that is representative of the resistance.

The flex sensor can have a length in a range between, e.g., 1 inch to 16 inches.

The angle of bending can represent an angle between a first portion of the flexible sleeve relative to a second portion of the flexible sleeve, and the sleeve tightening mechanism can be configured to tighten the flexible sleeve in response to the angle sensor detecting that the angle of bending is greater than a predetermined angle.

The sleeve tightening mechanism can be configured to apply a variable amount of force to tighten the flexible sleeve, and the force can be dependent on the angle of bending of the flexible sleeve. The controller can be configured to control the sleeve tightening mechanism to apply a larger force to tighten the flexible sleeve upon detecting that the measured angle of bending is greater than the reference angle of bending, and the greater the difference between the measured angle of bending and the reference angle of bending, the larger the force applied to tighten the flexible sleeve.

The controller can be configured to control the sleeve tightening mechanism to reduce an inner diameter of the flexible sleeve in response to the first sensor detecting that the angle of bending of the flexible sleeve is greater than the reference angle of bending of the flexible sleeve by a predetermined threshold.

The sleeve tightening mechanism can include at least one string and at least one motor that pulls the at least one string to tighten the flexible sleeve.

The flexible sleeve can have a first end and a second end, the flexible sleeve can extend from the first end to the second end, the first end can form a first opening, and the second end can form a second opening. The at least one motor can include at least a first motor and a second motor, the first motor can be positioned closer to the first end of the flexible sleeve as compared to the second motor, the second motor can be positioned closer to the second end of the flexible sleeve as compared to the first motor, and both the first and second motors can be configured to pull the at least one string to tighten the flexible sleeve.

The controller can be configured to control the at least motor to pull the at least one string to pull a first portion of the flexible sleeve to be closer to a second portion of the flexible sleeve to tighten the flexible sleeve.

The flexible sleeve can include a first set of eyelets and a second set of eyelets, the at least one string can pass through the first set of eyelets and the second set of eyelets, and the controller can be configured to control the at least one motor to pull the at least one string to pull at least some of the first set of eyelets closer to at least some of the second set of eyelets to tighten the flexible sleeve.

The at least one string can crisscrosses between the first set of eyelets and the second set of eyelets.

The flexible sleeve can include a first portion, a second portion, and a third portion, the controller can be configured to control the at least one motor to pull the at least one string to pull the first portion closer to the second portion based on the result of the comparison of the detected configuration of the flexible sleeve and the reference configuration of the flexible sleeve, and the third portion can be positioned under at least a portion of the at least one string.

The knee brace can be worn around a user's knee, and the third portion of the flexible sleeve can be positioned between the at least one string and the user's skin.

The first portion and the second portion can be parts of a first piece of fabric, and the third portion can be part of a second piece of fabric different from the first piece of fabric.

The first sensor can be disposed on an outer surface of the flexible sleeve or an inner surface of the flexible sleeve.

The first sensor can extend along a longitudinal direction of the flexible sleeve, and the first sensor can be configured to measure a bending of the flexible sleeve in the longitudinal direction.

The flexible sleeve can have a length in a range between, e.g., 4 inches to 16 inches.

The flexible sleeve can have an inner diameter in a range between, e.g., 3 inches to 10 inches.

The flexible fabric can include nylon, spandex, neoprene, or Drytex Phalanx.

The flexible fabric can include a breathable fabric or a moisture wicking fabric.

The can be configured to reduce a risk of anterior cruciate ligament tear for a user wearing the knee brace around a knee of the user.

The first sensor can be attached to a portion of the flexible sleeve positioned at a backside of the knee, and detecting the bending of the flexible sleeve can include detecting the bending of the portion of the flexible sleeve positioned at the backside of the knee.

Adjusting the tightness of the flexible sleeve can include tightening the flexible sleeve in response to detecting that the bending of the flexible sleeve is greater than a predetermined angle relative to a reference configuration of the flexible sleeve.

The predetermined angle can be, e.g., in a range between 5° and 10°.

The method can include applying a variable amount of force to tighten the flexible sleeve, in which the force is dependent on an amount of bending of the flexible sleeve. Applying the variable amount of force can include applying a larger force to tighten the flexible sleeve upon detecting a larger amount of bending of the flexible sleeve, and applying a smaller force to tighten the flexible sleeve upon detecting a smaller amount of bending of the flexible sleeve.

The method can include estimating an amount of bending of the knee based on a detected amount of bending of the flexible sleeve, and tightening the flexible sleeve based on the estimated amount of bending of the knee.

The first sensor can include a flex sensor that is configured to have a resistance that varies in accordance to an amount of bending, and detecting the bending of the flexible sleeve can include measuring the resistance of the flex sensor.

Detecting the bending of the flexible sleeve can include detecting an angle between a first portion of the flexible sleeve relative to a second portion of the flexible sleeve.

In some examples, adjusting the tightness of the flexible sleeve around the knee can include reducing an inner diameter of the flexible sleeve to tighten the flexible sleeve around the knee. In some examples, adjusting the tightness of the flexible sleeve can include pulling at least one string to tighten the flexible sleeve.

Pulling the at least one string can include operating at least one motor to pull the at least one string.

The flexible sleeve can have a first end and a second end, the flexible sleeve can extend from the first end to the second end, the first end can form a first opening, and the second end can form a second opening. Wearing the flexible sleeve around the knee can include extending a thigh of the user through the first opening and extending a lower leg of the user through the second opening. The at least one motor can include at least a first motor and a second motor, the first motor can be positioned closer to the first end of the flexible sleeve as compared to the second motor, and the second motor can be positioned closer to the second end of the flexible sleeve as compared to the first motor. Operating the at least one motor to pull the at least one string can include using both the first and second motors to pull the at least one string.

The flexible sleeve can include a first edge and a second edge. Pulling the at least one string to tighten the flexible sleeve can include pulling the at least one string to pull the first edge closer to the second edge or increase an overlap between the first edge and the second edge to tighten the flexible sleeve.

The knee brace can include a first set of eyelets and a second set of eyelets attached to the flexible sleeve, and the at least one string can pass through the first set of eyelets and the second set of eyelets. Pulling the at least one string to tighten the flexible sleeve can include pulling the at least one string to pull at least some of the first set of eyelets closer to at least some of the second set of eyelets to tighten the flexible sleeve.

The method can include crisscrossing the at least one string between the first set of eyelets and the second set of eyelets.

The method can include receiving a sensor signal from the first sensor, comparing the sensor signal with a reference signal, and adjusting the tightness of the flexible sleeve around the knee based on the comparison between the sensor signal and the reference signal.

The method can include disposing a cushion layer between at least a portion of the at least one string and a skin of the user.

The method can include disposing the first sensor on an outer surface of the flexible sleeve, or on an inner surface of the flexible sleeve.

The method can include extending the first sensor along a longitudinal direction of the flexible sleeve, and measuring a bending of a first portion of the flexible sleeve relative to a second portion of the flexible sleeve.

In another general aspect, a system includes a knee brace, in which the knee brace includes a flexible sleeve having a flexible fabric; a memory device configured to store a reference bending angle of the flexible sleeve and a first threshold angle value; and a first sensor configured to measure a bending angle of the flexible sleeve. The knee brace includes a sleeve tightness adjustment mechanism configured to adjust a tightness of the flexible sleeve; and a controller configured to receive a first measurement signal from the first sensor, compare a first measured bending angle of the flexible sleeve with the reference bending angle of the flexible sleeve, and control the sleeve tightness adjustment mechanism to increase a tightness of the flexible sleeve in response to determining that the measured bending angle is larger than the reference bending angle by an amount greater than the first threshold angle.

Implementations of the aspects above can include one or more of the following features. The memory device can be configured to also store a second threshold angle value. The controller can be configured to, after the flexible sleeve has been tightened, receive a second measurement signal from the first sensor, compare a second measured bending angle of the flexible sleeve with the reference bending angle of the flexible sleeve, and control the sleeve tightness adjustment mechanism to reduce a tightness of the flexible sleeve in response to determining that the measured bending angle is either (i) smaller than the reference bending angle, or (ii) larger than the reference bending angle by an amount no greater than the second threshold angle.

The controller can be configured to perform a calibration procedure to determine the reference configuration, and store the reference configuration in the memory device.

The controller can be configured to perform the calibration procedure to determine a reference angle of bending of the flexible sleeve when the knee brace is worn by a user in a reference position.

The sleeve tightness adjustment mechanism can be configured to apply a variable amount of force to tighten the flexible sleeve, and the force can be dependent on the angle of bending of the flexible sleeve. The controller can be configured to control the sleeve tightening mechanism to apply a larger force to tighten the flexible sleeve upon detecting that the measured angle of bending is greater than a sum of the reference angle of bending and the first threshold angle, and the greater the difference between the measured angle of bending and the sum of the reference angle of bending and the first threshold angle, the larger the force applied to tighten the flexible sleeve.

The sleeve tightness adjustment mechanism can include at least one string and at least one motor that pulls the at least one string to tighten the flexible sleeve.

The system can further include a mobile computing device in wireless communication with the knee brace. In some examples, the mobile computing device can include a user interface that enables a user to set the first threshold angle value. In some examples, the mobile computing device can include a user interface that enables a user to view information derived from measurements of the first sensor.

Other features, objects, and advantages of the invention will be apparent from the description and drawings, and from the claims.

DETAILED DESCRIPTION

This description relates in general to an active knee brace for supporting a knee of a user, in which the knee brace includes a sleeve that is worn around the knee, a sensor for detecting an angle of bending of the knee, and an active tightening mechanism configured to tighten the sleeve to provide additional support to the user's knee based on the detected bending angle. In some implementations, the sensor includes a thin elongated flex sensor that is attached to the sleeve. The tightening mechanism includes, for example, one or more strings or a lacing system, and a tensioning system that includes one or more motors for adjusting a tension of the one or more strings or the lacing system to tighten or loosen the sleeve as needed.

Figure 1A:
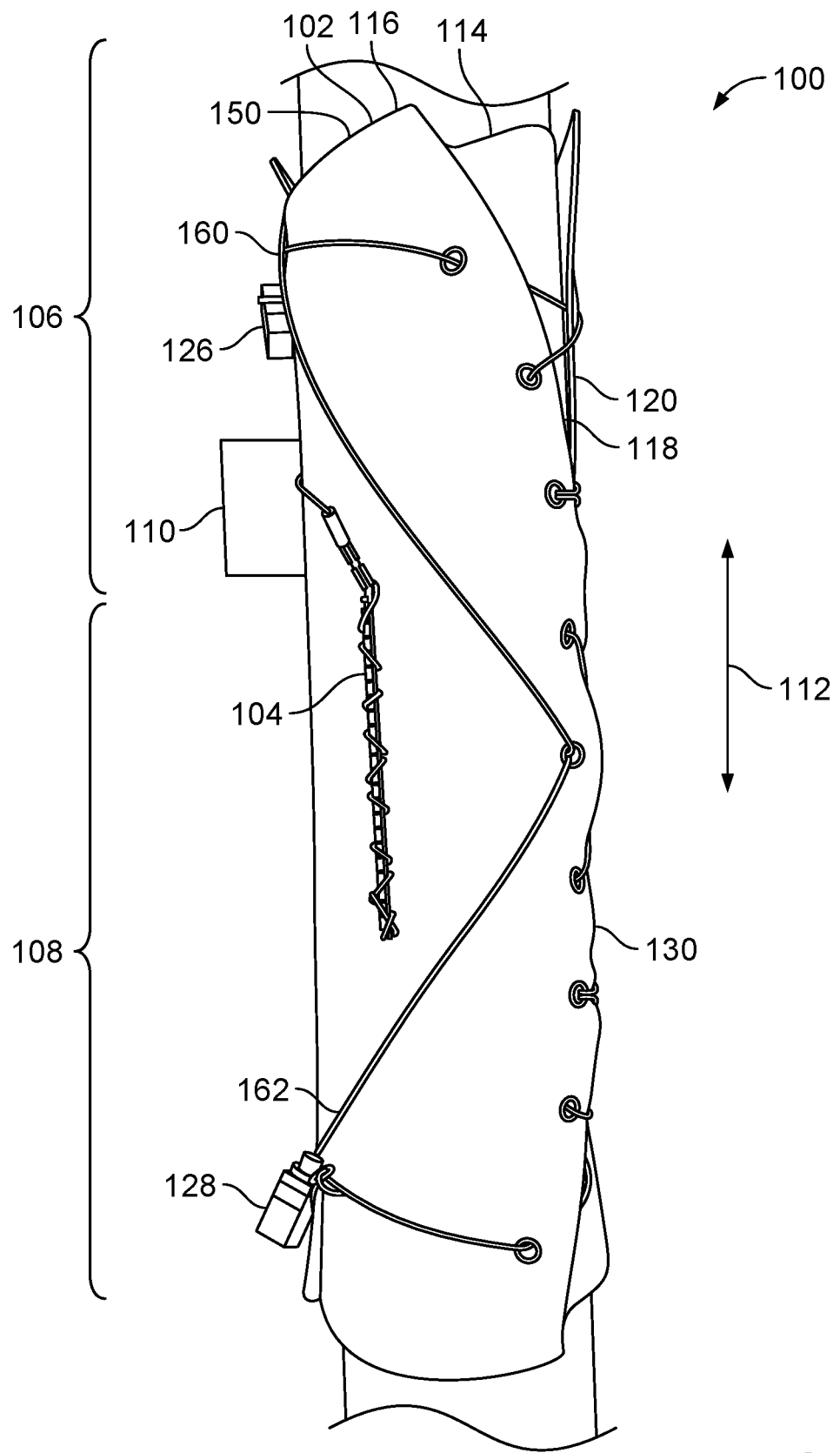
FIGS. 1A and 1B are diagrams of a first example of a knee brace.
Figure 1B:
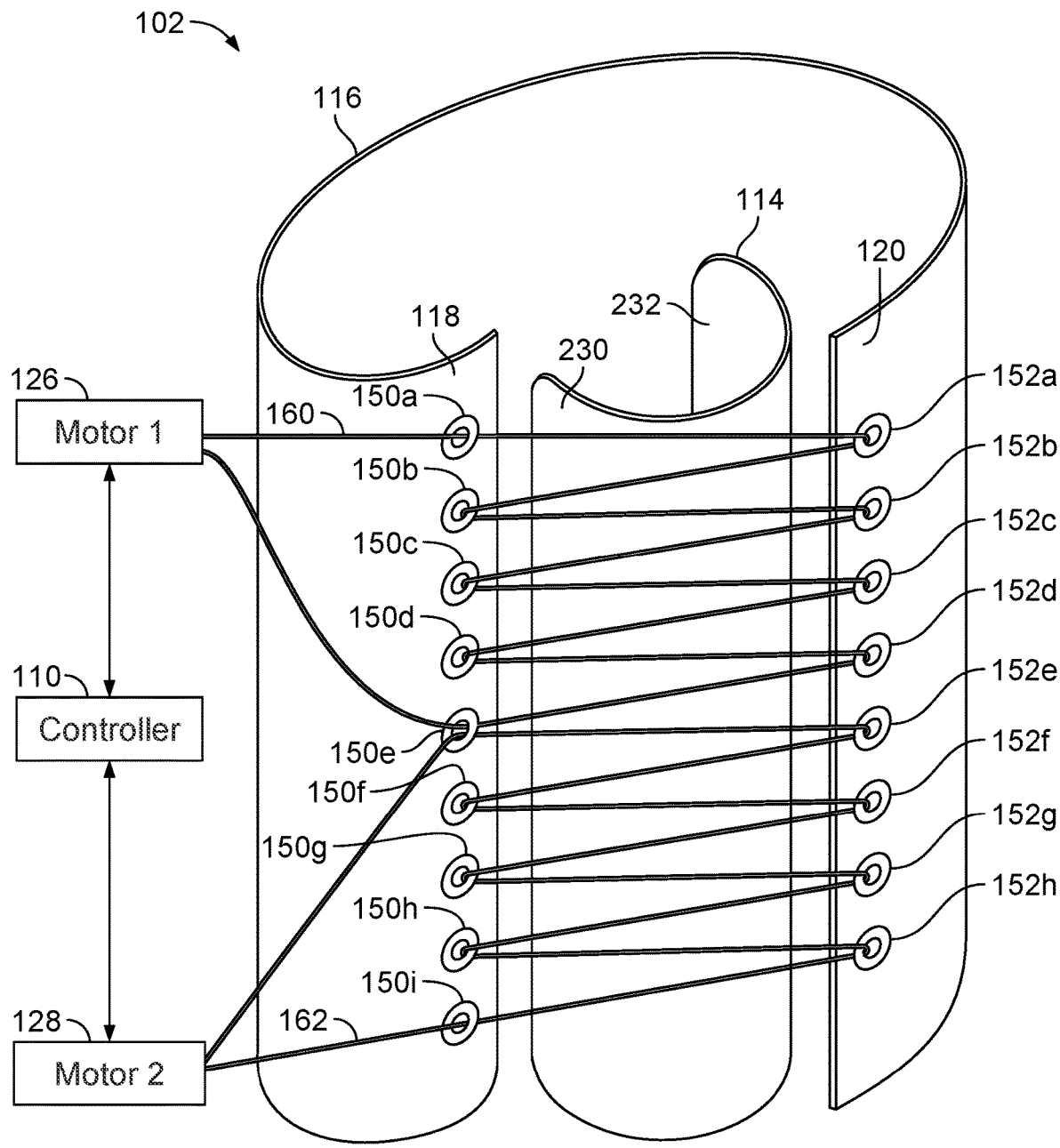

Referring to FIGS. 1A and 1B, a knee brace 100 includes a flexible sleeve 102 that is made of a flexible fabric and a sleeve tightening mechanism to adjust a tightness of the flexible sleeve 102. The flexible fabric can be, e.g., nylon, spandex, or neoprene. A sensor 104 is provided for detecting a configuration of the flexible sleeve 102, such as a bending between an upper portion 106 of the flexible sleeve 102 and a lower portion 108 of the flexible sleeve 102. When the sensor 104 detects that the flexible sleeve 102 is bent in a way that indicates the knee is bent in a vulnerable position, a controller adjusts the sleeve tightening mechanism to increase a tightness of the flexible sleeve 102 to provide additional support for the knee to prevent the knee from further bending abnormally. This reduces the amount of time that the anterior cruciate ligament is in a vulnerable position and thus may reduce the likelihood of anterior cruciate ligament tear.

In some implementations, the flexible sleeve 102 includes a first piece of fabric 114 and a second piece of fabric 116 that together form a tubular configuration that wrap around the knee. The first piece of fabric 114 forms an inner sleeve member and wraps around at least a portion of the knee, and the second piece of fabric 116 forms an outer sleeve member that wraps around at least a portion of the knee and overlaps a least a portion of the first piece of fabric 114. As will be described in more detail below, the sleeve tightening mechanism is configured to tighten the second piece of fabric 116 so that the second piece of fabric 116 provide additional support for the knee. The first piece of fabric 114 functions as a cushion between components of the sleeve tightening mechanism and the user's skin so that the knee brace is comfortable to use. The components in the figures are intended to illustrate the features of the invention and may not be drawn to scale.

For example, the first piece of fabric 114 can wrap around the front half of the knee. The second piece of fabric 116 can wrap around about 80% to 90% of the knee, leaving the front 20% to 10% of the knee open. In this example, the second piece of fabric 116 has a first edge portion 118 and a second edge portion 120 that are spaced apart from each other. The knee brace 100 operates between a normal state and a tightened state. In the normal state, the flexible sleeve 102 provides a normal amount of support to the knee due to the elasticity of the flexible fabric. In the tightened state, the sleeve tightening mechanism pulls the first edge portion 118 and the second edge portion 120 of the second piece of fabric 116 closer together, reducing the diameter of the flexible sleeve 102, causing the flexible sleeve 102 to become tighter and provide more support to the knee. In some examples, the sleeve tightening mechanism pulls first edge portion 118 and the second edge portion 120 of the second piece of fabric 116 closer together so that they overlap, reducing the diameter of the flexible sleeve 102, causing the flexible sleeve 102 to become tighter and provide more support to the knee.

The first piece of fabric 114 has a first edge portion 230 and a second edge portion 232. For example, the first edge portion 230 of the first piece of fabric 114 is attached (e.g., sewn or glued) to the first edge portion 118 of the second piece of fabric 116. The second edge portion 120 of the second piece of fabric 116 can move relative to a second edge portion 232 of the first piece of fabric 114. When the second piece of fabric 116 is tightened or loosened by the knee brace tightening mechanism, the second edge portion 120 of the second piece of fabric 116 moves relative to the second edge portion 232 of the first piece of fabric 114.

The controller 110 determines when the knee brace 100 operates in the normal state and when the knee brace 100 operates in the tightened state based on an output signal of the sensor 104. In some implementations, the sensor 104 is an elongated flex sensor that is attached to the flexible sleeve 102 and extend parallel to a longitudinal direction 112 of the flexible sleeve 102. For example, the knee brace 100 is worn around the knee and positioned such that the flex sensor 104 is positioned at a backside of the knee and extends from a position above the knee to a position below the knee. This way, when the knee bends, the flexible sleeve 102 will bend along with the knee, and the flex sensor 104 will also bend along with the flexible sleeve 102. The amount of bending of the flex sensor 104 indicates the amount of bending of the flexible sleeve 102, which in turn indicates the amount of bending of the knee.

In some implementations, the sleeve tightening mechanism includes one or more motors that pulls one or more strings or lace to tighten the flexible sleeve 102. In this example, a first motor 126 and a second motor 128 are provided to pull at least one string 130 or lace to tighten the flexible sleeve 102. For example, the first and second motors 126, 128 can be servo motors or stepper motors. Each motor can have a rotating shaft, in which the motor winds the corresponding string or lace around the shaft to tighten the flexible sleeve 102, and later unwinds the string or lace to loosen the flexible sleeve 102. The at least one string 130 can be made of, e.g., size B thread. The flexible sleeve 102 forms a first opening at the top of the flexible sleeve 102 and a second opening at the bottom of the flexible sleeve 102. The first opening allows the thigh to pass through, and the second opening allows the lower leg to pass through. The first motor 126 is positioned near the top of the sleeve and closer to the first opening (as compared to the second motor 128), and the second motor 128 is positioned near the bottom of the sleeve and closer to the second opening (as compared to the first motor 126). By using two motors to pull the string 130 in parallel, the string 130 can be pulled faster to cause the flexible sleeve 102 to be tightened more quickly.

In some implementations, the flexible sleeve 102 includes a first set of eyelets, e.g., 150a to 150i collectively referenced as 150, and a second set of eyelets, e.g., 152a to 152h collectively referenced as 152, in which the at least one string 130 passes through the first set of eyelets 150 and the second set of eyelets 152. In this example, the first set of eyelets 150 are positioned near the first edge portion 118 of the second piece of fabric 116, and the second set of eyelets 152 are positioned near the second edge portion 120 of the second piece of fabric 116. The controller 110 is configured to control the first motor 126 and the second motor 128 to pull the at least one string 130 to pull at least some of the second set of eyelets 152 closer to at least some of the first set of eyelets 150, which in turn pulls the second edge portion 120 of the second piece of fabric 116 closer to the first edge portion 118 of the second piece of fabric 116 to tighten the flexible sleeve 102.

In this example, the at least one string 130 crisscrosses between the first set of eyelets 150 and the second set of eyelets 152. For example, two strings can be used in which a first string 160 tightens the upper portion of the flexible sleeve 102, and a second string 162 tightens the lower portion of the flexible sleeve 102. For example, the first string 160 passes the eyelets 150a, 152a, 150b, 152b, 150c, 152c, 150d, 152d, and 150e in sequence. The second string 162 passes the eyelets 150e, 152e, 150f, 152f, 150g, 152g, 150h, 152h, and 150i in sequence. The first string 160 is pulled by the first motor 126, and the second string 162 is pulled by the second motor 128. When the first motor 126 pulls the first string 160, the eyelets 152a, 152b, 152c, and 152d are pulled toward the eyelets 150a, 150b, 150c, 150d, and 150e. When the second motor 128 pulls the second string 162, the eyelets 152e, 152f, 152g, and 152h are pulled toward the eyelets 150e, 150f, 150g, 150h, and 150i. The actions of the motors 126 and 128 cause the flexible sleeve 102 to be tightened. In some examples, a single motor and a single string can be used to tighten the flexible sleeve 102.

The tightening mechanism can have other configurations. The routing of the one or more strings through the eyelets can be different from the example shown in FIG. 1B. The number of eyelets used for the knee brace 100 can be greater or less than the number of eyelets shown in FIG. 1B. Instead of using eyelets, string or lace guides can be attached to the flexible fabric to help guide the string(s) or lace. After the knee brace 100 enters a tightened state, the controller 110 continues to determine the configuration of the flexible sleeve 102, i.e., the angle of bending of the flexible sleeve 102, which indicates the bending of the knee. When the controller 110 determines that the configuration of the flexible sleeve 102 returns to normal, i.e., the bending angle of the flexible sleeve 102 corresponds to normal bending of the knee, the controller 110 controls the motors 126 and 128 to loosen the strings 160 and 162 so that the flexible sleeve 102 returns to the normal state, allowing free movement of the knee.

For example, the flexible sleeve 102 can have a length (measured along the longitudinal direction 112) in a range between, e.g., 4 inches to 16 inches and configured to cover the knee, a portion of the thigh above the knee, and a portion of the lower leg below the knee when the flexible sleeve 102 is worn by the user. The flexible sleeve 102 can have an inner diameter in a range between, e.g., 3 inches to 10 inches when operating in the normal state. The flex sensor 104 can have a length in a range between, e.g., 1 inch to 12 inches. These are merely examples, the length and inner diameter of the flexible sleeve 102 and the length of the flex sensor 104 can be different from the ones described above.

The knee brace 100 includes a power source (not shown) that provides power to the controller 110, the sensor 104, and the motors 126, 128. For example, the power source can be a battery. For example, the power source can include a smaller electric generator that generates electricity from the kinetic motion of the user.

Figure 2C:
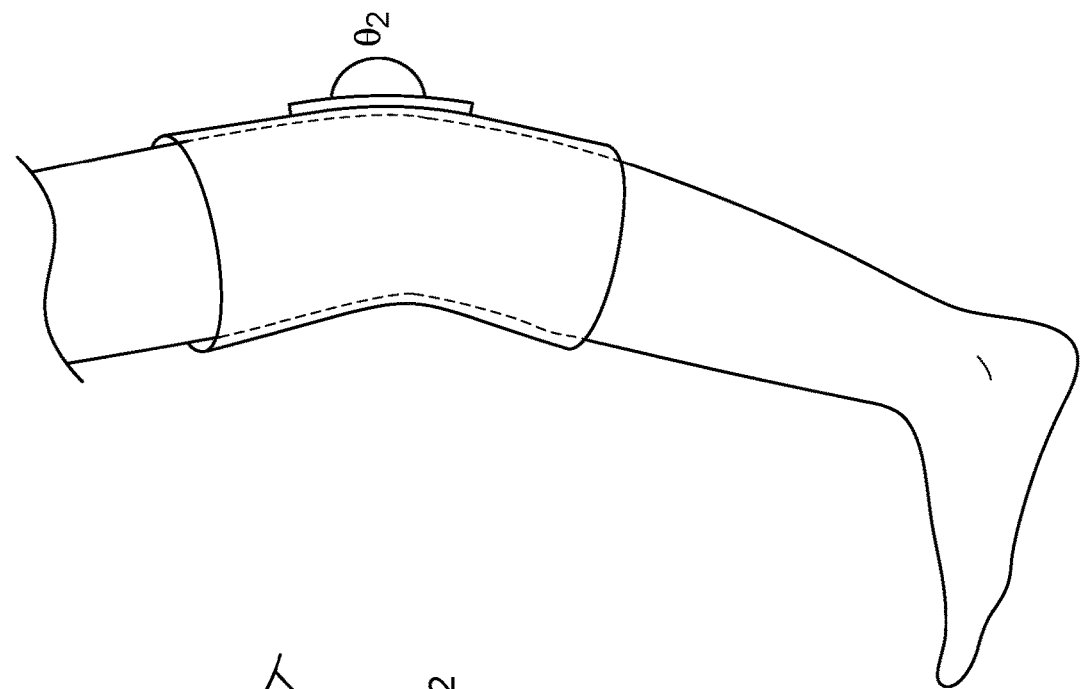
FIGS. 2A to 2C are diagrams showing a knee brace worn on a knee in various configurations.
Figure 2B:
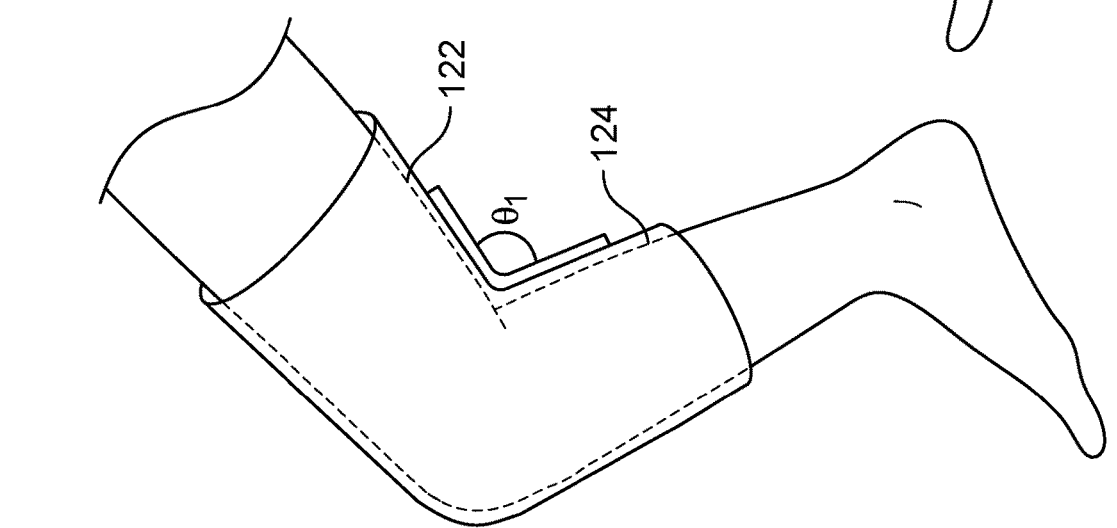
Figure 2A:
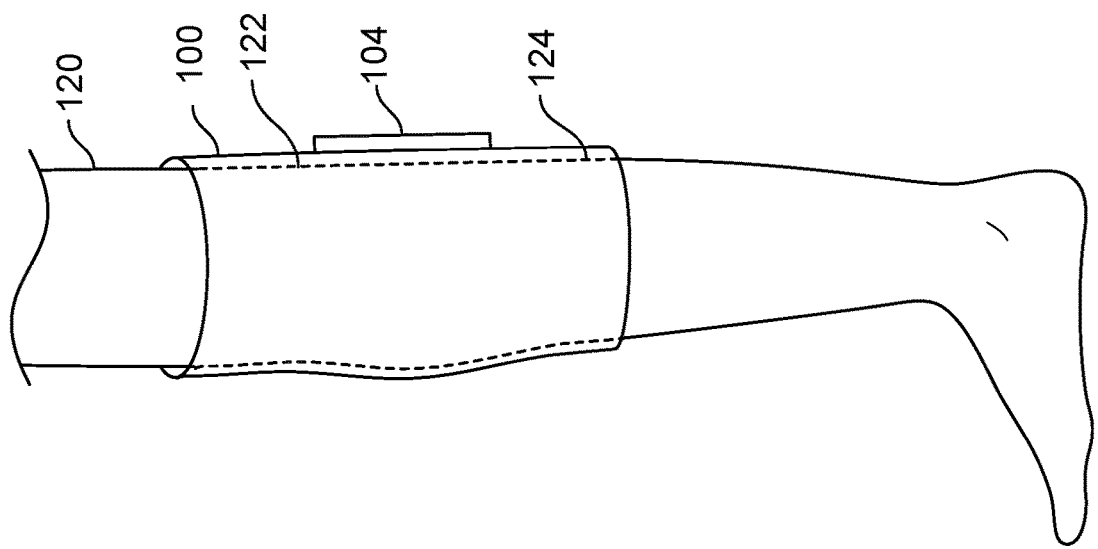

FIG. 2A is a diagram of an example in which the knee brace 100 is worn around the knee and the flex sensor 104 is positioned at a backside of the knee. In the example of FIG. 2A, the leg 120 is extending straight, i.e., the backside of the thigh 122 above the knee and the backside of the lower leg 124 below the knee are in a straight line, and the flex sensor 104 extends in a straight line and is not bent.

FIG. 2B is a diagram of an example in which the knee is bent in a normal manner. In this example, the backside of the thigh 122 above the knee and the backside of the lower leg 124 below the knee form an angle less than 180°, causing the flex sensor 104 to be bent at an angle θ1 in which θ1≤180°. For example, when the angle θ1 is 180° or less, the knee brace 100 operates in the normal state and the sleeve tightening mechanism does not tighten the flexible sleeve 102.

FIG. 2C is a diagram of an example in which the knee is bent in an abnormal manner. In this example, the backside of the thigh 122 above the knee and the backside of the lower leg 124 below the knee form an angle greater than 180°, causing the flex sensor 104 to be bent at an angle θ2 in which θ2>180°. This can occur when the user is, e.g., engaged in field or court sports and performs one step-stops, cutting tasks, sudden changes of direction, landing from a jump with inadequate knee and hip flexion (at or near full extension), a lapse of concentration due to an unanticipated event of a change in the direction of play, or a deceleration maneuver combined with a change of direction while the foot is in a closed chain position.

For example, when the angle θ of the backside of the flex sensor 104 is more than 180°, the knee brace 100 operates in a tightened state and the controller 110 controls the sleeve tightening mechanism to tighten the flexible sleeve 102 to provide additional support to the knee. Providing additional support to the knee can slow down the rate of additional abnormal bending of the knee, prevent further abnormal bending of the knee, and/or provide a restoring force to help the knee to return to a normal configuration, and thereby reduce the risk of anterior cruciate ligament injury. A feature of the knee brace 100 is that it can reduce the amount of time that the knee is in a vulnerable position that may result in anterior cruciate ligament injury.

Figure 3:
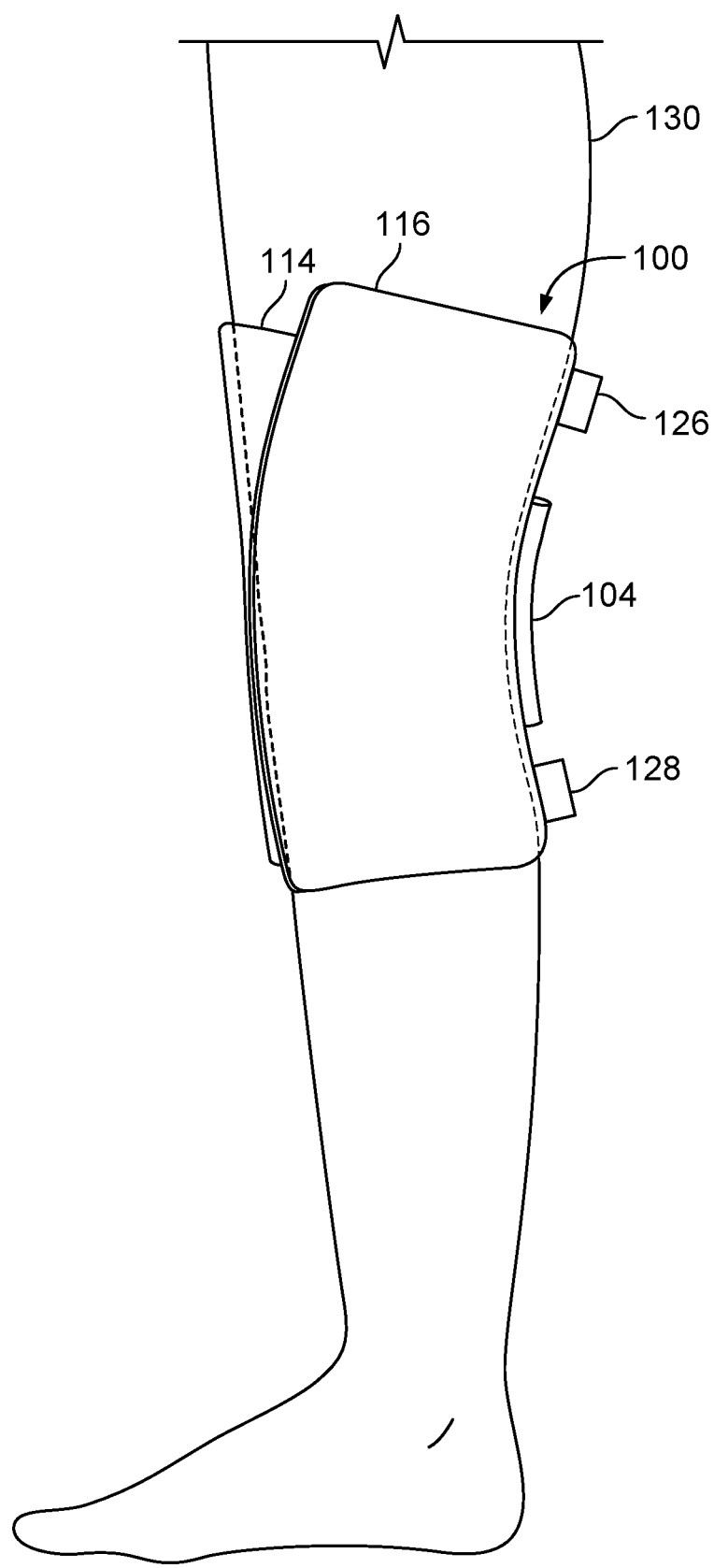
FIG. 3 is a diagram showing a knee brace worn on a knee.

Referring to FIG. 3, when a user's leg is viewed from the side, the backside of the leg often does not form a straight line at the knee joint, but rather is curved in a way that may be different among different users. In some implementations, the knee brace 100 has a calibration function that allows the user to measure the configuration of the flex sensor 104 when the user's knee is in a reference configuration, or a normal configuration, such as when the knee has a full extension, in which the leg can be extending straight or slightly at an angle, depending on the user. In some examples, the user extends the knee forward fully in a comfortable manner without too much force, and records the configuration of the flex sensor 104 as the reference configuration or reference angle. In this example, the flex sensor 104 is configured to measure one degree of freedom, in which the bending angle of the flex sensor 104 is measured and stored as a reference angle $\theta_{ref}$. For example, the knee brace 100 can include a storage device, such as a flash memory device, that stores the reference angle $\theta_{ref}$. Afterwards, when the user engages in sports activities, the controller 110 periodically samples the measured bending angle $\theta_{measure}$ of the flex sensor 104 and compares the measured bending angle $\theta_{measure}$ with the reference angle $\theta_{ref}$ to determine whether the knee brace 100 should operate in the normal state or the tightened state.

For example, if the measured bending angle is equal to or smaller than the reference angle, $\theta_{measure} \leq \theta_{ref}$, then the controller 110 determines that the knee brace 100 should operate in the normal state. If the measured bending angle is greater than the reference angle, $\theta_{measure} > \theta_{ref}$, then the controller 110 determines that the knee brace 100 should operate in the tightened state, and controls the sleeve tightening mechanism to tighten the flexible sleeve 102 to provide additional support for the knee. This way, the knee brace 100 can provide additional support for the knee when the knee is about to become vulnerable by bending in an abnormal degree that may increase the risk of anterior cruciate ligament tear. The knee brace 100 allows free movement of the knee under normal circumstances. Because the knee brace 100 does not interfere with an athlete's movement during normal situations, this increases the likelihood that the athlete will actually wear the knee brace 100 during sports events.

In some implementations, the knee brace 100 is configured to allow the knee to bend beyond the reference angle by a first predetermined threshold value $\theta_{threshold1}$ before the knee brace enters the tightened state. The knee brace operates in the normal state when $\theta_{measure} \leq \theta_{ref} + \theta_{threshold1}$. If the measured bending angle is greater than the reference angle by an amount greater than the first threshold value $\theta_{threshold1}$, i.e., $\theta_{measure} > \theta_{ref} + \theta_{threshold1}$, then the controller 110 determines that the knee brace 100 should operate in the tightened state, and controls the sleeve tightening mechanism to tighten the flexible sleeve 102 to provide additional support for the knee. For example, the threshold angle can be 0°, 1°, 2°, 3°, 4°, 6°, 7°, 8°, 9°, or 10°.

After the sleeve 102 is tightened, the controller 110 continues to monitor the knee bending angle. If the angle past full knee extension is less than a second threshold angle, the knee brace is loosened by controlling the motors. For example, if $\theta_{measure}<\theta_{ref}+\theta_{threshold2}$, the knee brace is loosened. For example, the second threshold angle can be in a range from −1° to 4°, or in a range from −1° to the first threshold angle $\theta_{threshold1}$.

The sleeve tightening mechanism is a sleeve tightness regulation mechanism that regulates the tightness of the sleeve according to measurements from sensors of the knee brace 100. When a lacing system is used to adjust the distance between the first edge portion 118 and the second edge portion 120, a tensioning system is used to adjust the tension in the lacing system, which in turn adjusts the tightness of the sleeve 102.

In some implementations, the flex sensor 104 is configured to have a resistance that varies in accordance to the angle of bending of the flex sensor 104, which indicates the angle of bending of the flexible sleeve 102, which in turn indicates the angle of bending of the knee. The controller 110 determines the resistance of the flex sensor 104 based on an output signal from the flex sensor 104.

Figure 4:
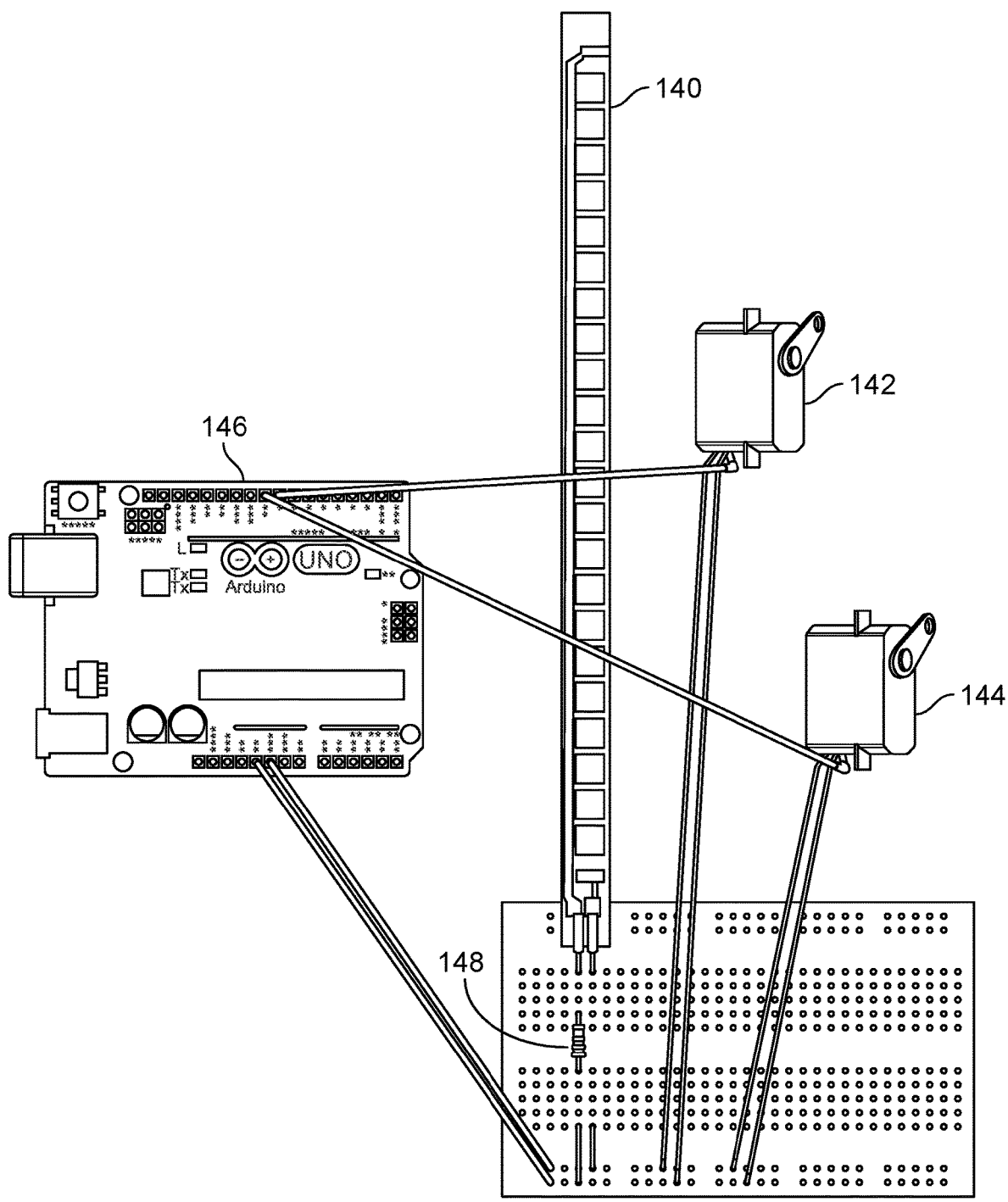
FIG. 4 is a diagram of a controller, motors, and a flex sensor.

FIG. 4 is a diagram that shows an example of a flex sensor 140, an example of a first motor 142, an example of a second motor 144, and an example of a controller 146. The figure shows an example in which the flex sensor 140, the motors 142 and 144, and the controller 146 are electrically coupled through a breadboard. In some implementations, the flex sensor 140, the motors 142 and 144, and the controller 146 can be electrically coupled using a printed circuit board. The controller 146 can be implemented as an integrated circuit. Additional components, such as memory devices and communication devices, can be integrated with the controller integrated circuit or mounted on the printed circuit board.

As shown in the figure, the flex sensor 140 is series connected with a resistor 148, e.g., a 47 kΩ resistor.

Figure 5:
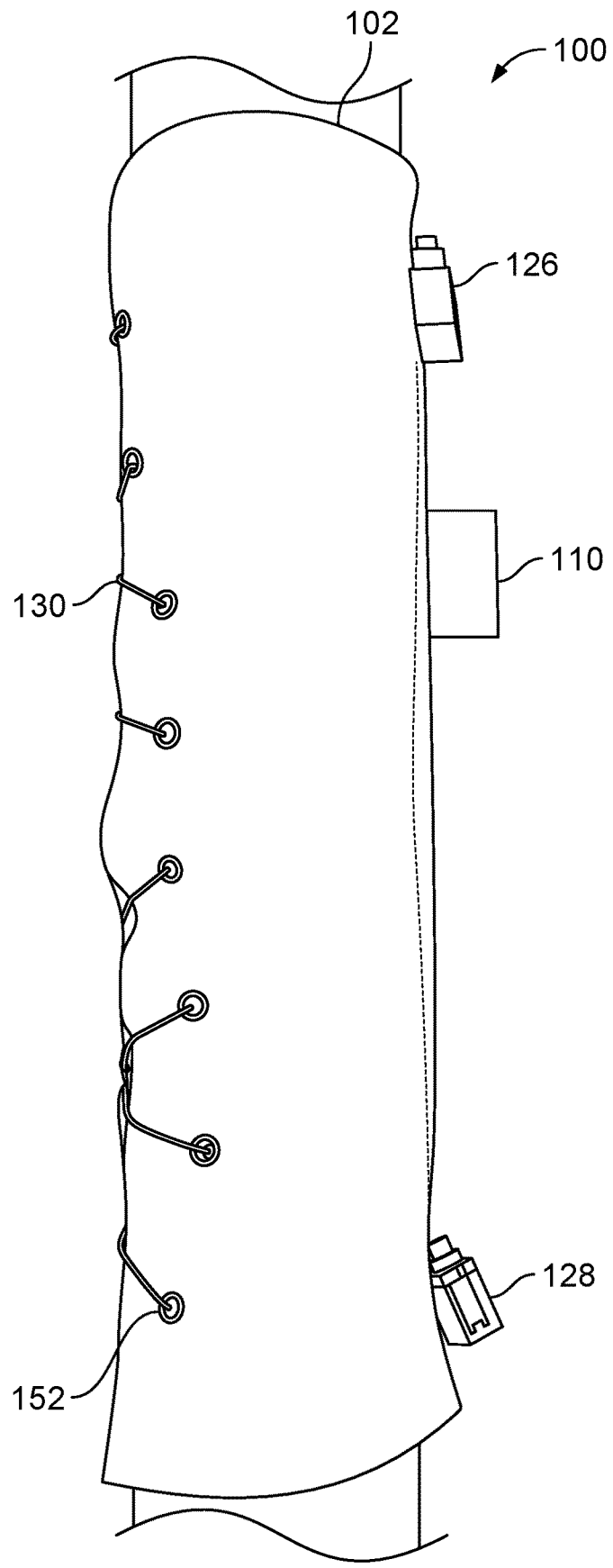
FIGS. 5 and 6 are diagrams of additional views of the first example of the knee brace.

FIG. 5 shows a side view of the knee brace 100. The controller 110 and the motors 126 and 128 can be attached to the flexible sleeve 102 using any method. For example, pouches can be sewn to the flexible sleeve 102, and the controller 110 and the motors 126 and 128 can be placed in the pouches. In some examples, the electrical connections between the controller 110 and the motors 126 and 128 can be embedded in the flexible fabric 116 or be covered using another piece of flexible fabric.

Figure 6:
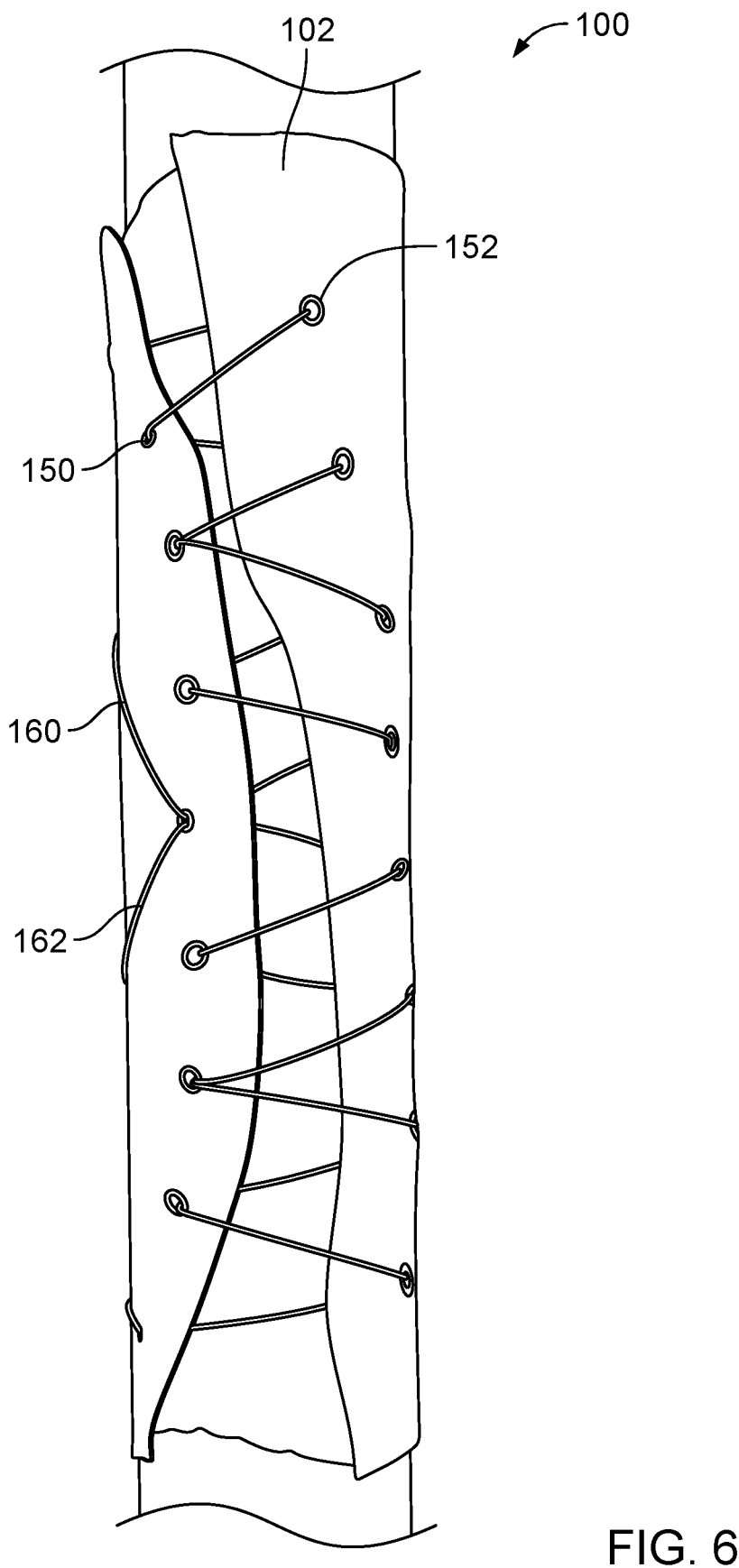

FIG. 6 shows a front view of the knee brace 100.

Figure 7:
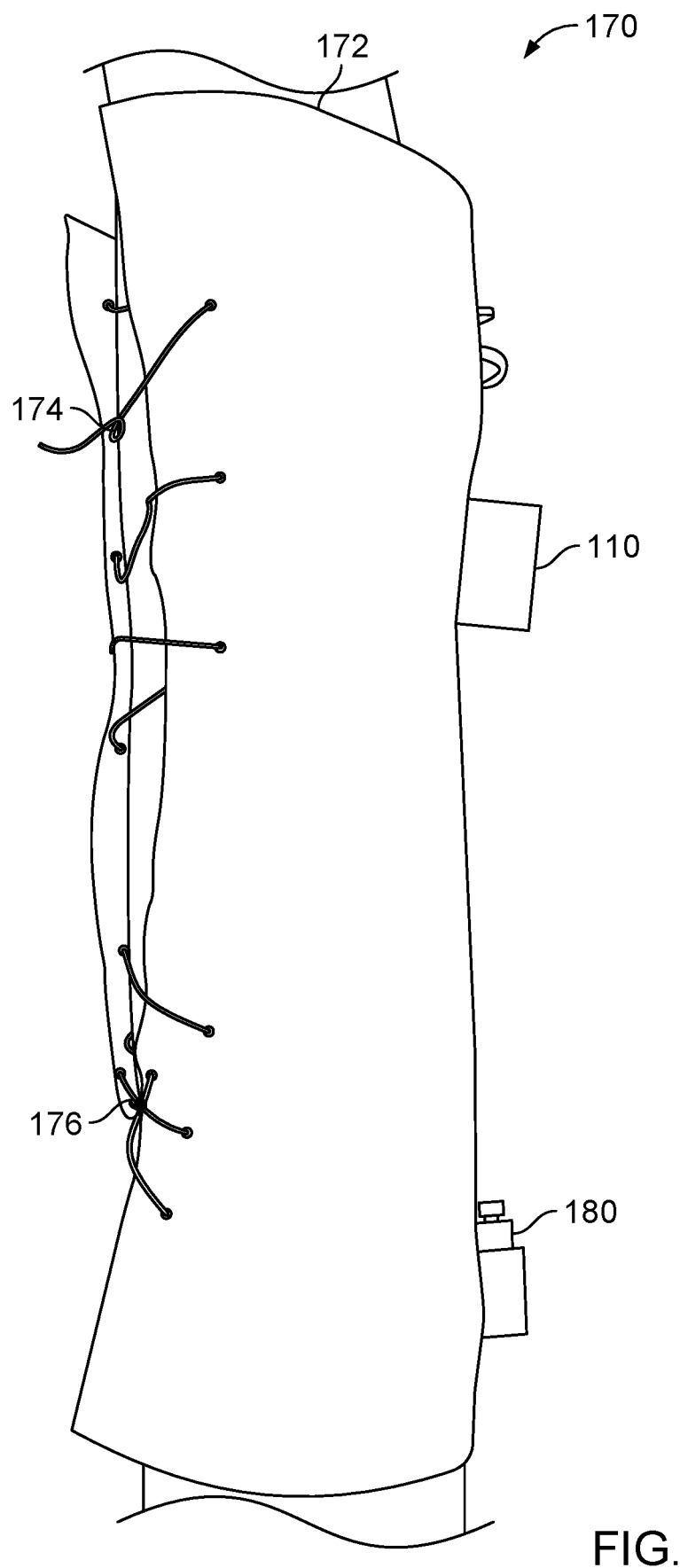
FIGS. 7 to 9 are diagrams of a second example of a knee brace.

FIG. 7 is a diagram of an example knee brace 170 that includes a flexible sleeve 172 that is configured to be worn around a user's knee. The knee brace 170 includes at least one yarn that is used to tighten the flexible sleeve 172. In this example, the at least one yarn includes a first yarn 174 for tightening an upper portion of the flexible sleeve 172 and a second yarn 176 for tightening a lower portion of the flexible sleeve 172. A first motor 178 is configured to pull the first yarn 174, and a second motor 180 is configured to pull the second yarn 176, to tighten the flexible sleeve 172. The first motor 178 and the second motor 180 are controlled by a controller 110.

Figure 8:
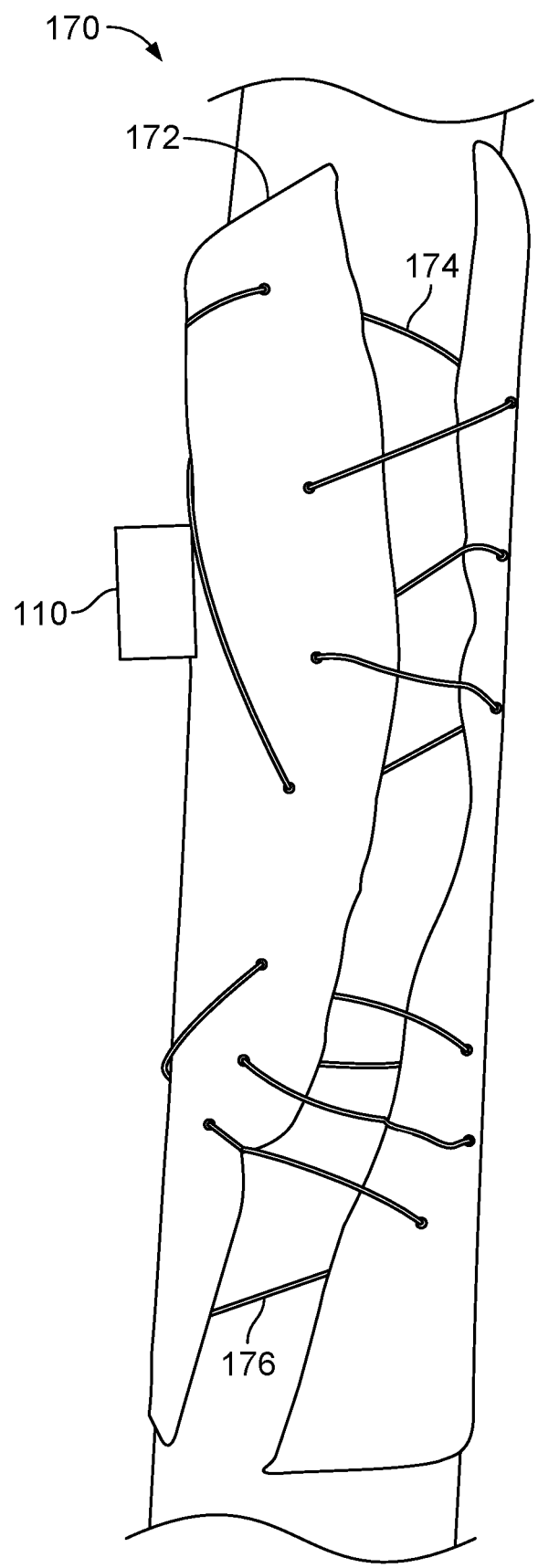
Figure 9:
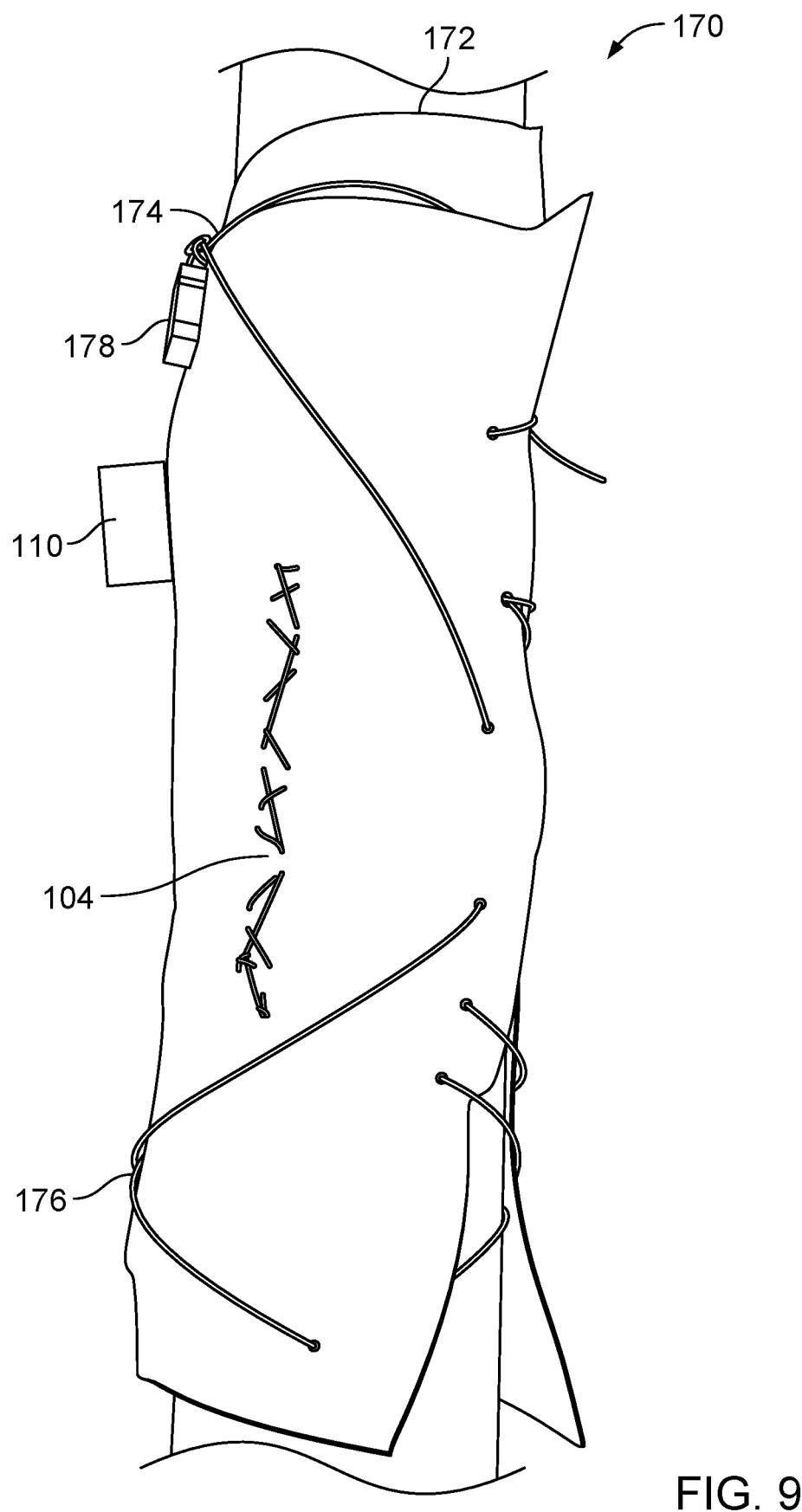

FIGS. 8 and 9 show additional views of the knee brace 170.

Figure 10:
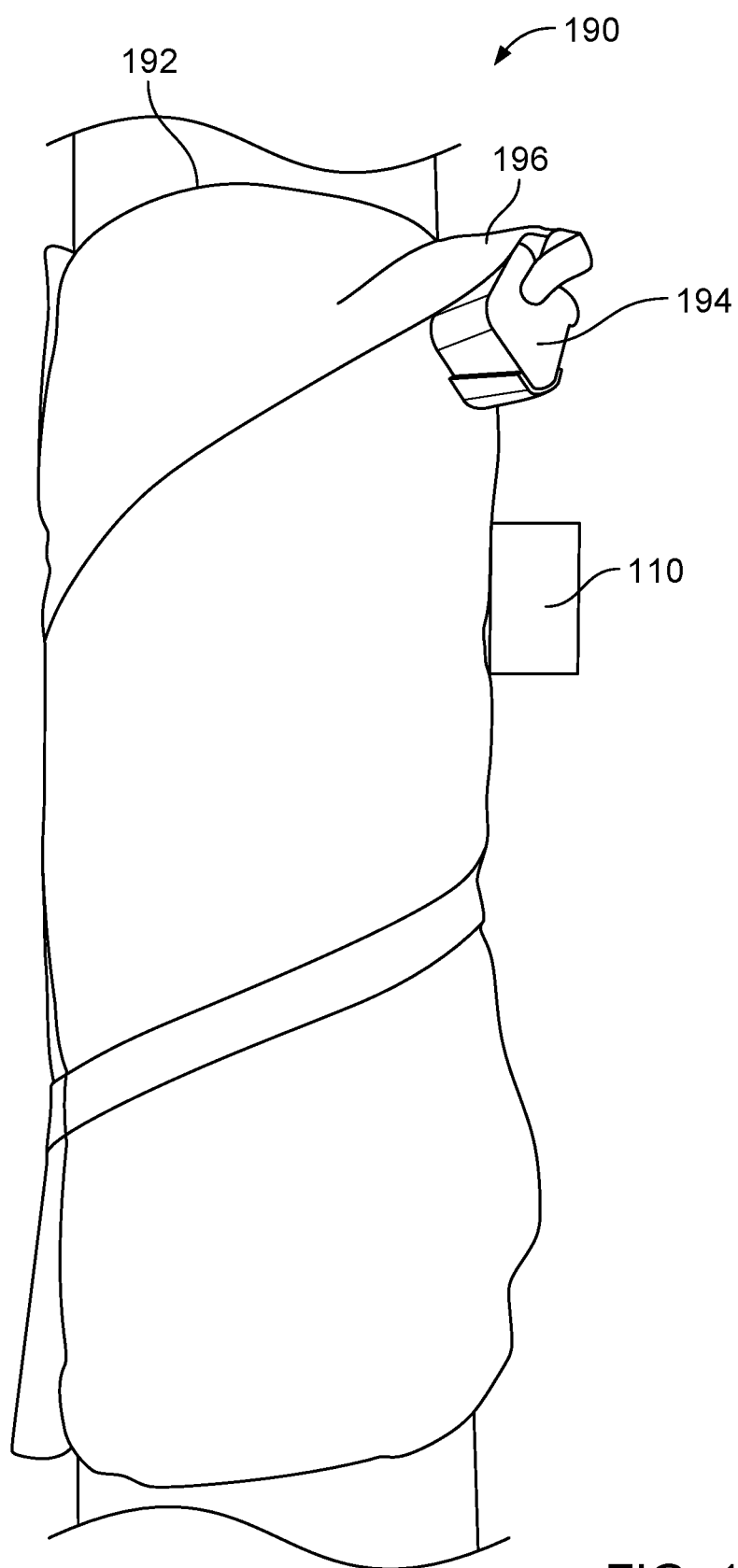
FIGS. 10 to 12 are diagrams of a third example of a knee brace.

FIG. 10 is a diagram of an example knee brace 190 that includes a flexible sleeve 192 that is configured to be worn around a user's knee. The knee brace 190 includes a stepper motor 194 that is attached to the top right of the brace 190. In this example, a 0.5-inch by 15-inch piece of Neoprene fabric 196 is wrapped around the brace twice in which one end of the fabric 196 is attached to the stepper motor 194 and another end of the fabric 196 is attached to the bottom right corner of the brace. A flex sensor 104 is attached to the middle back of the brace 190 so that the flex sensor 104 is on the anterior of the knee when in use. The stepper motor 194 is configured to pull the fabric 196 to tighten the brace 190. A controller 110 controls the stepper motor 194 based on the output signals of the flex sensor 104.

Figure 11:
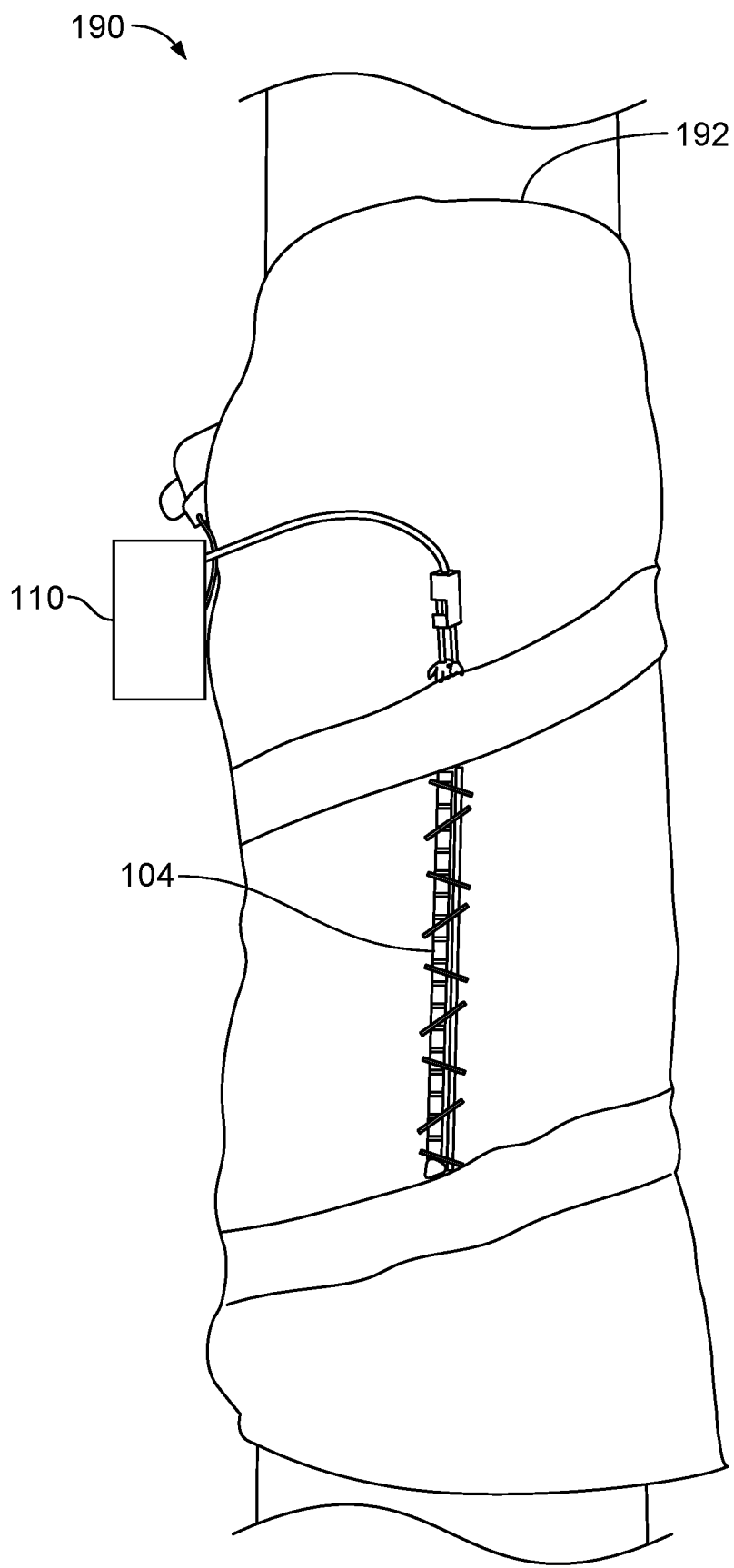
Figure 12:
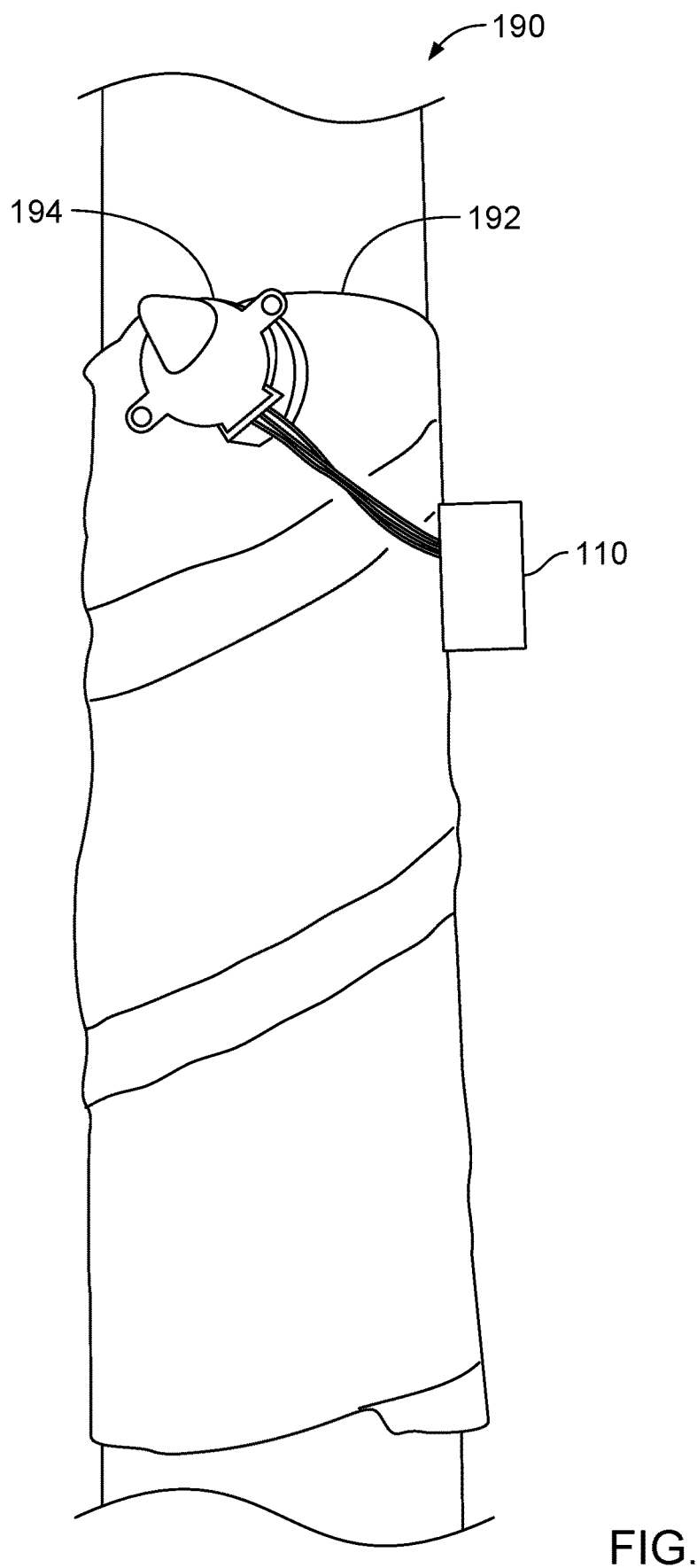

FIGS. 11 and 12 show additional views of the knee brace 190.

Figure 13:
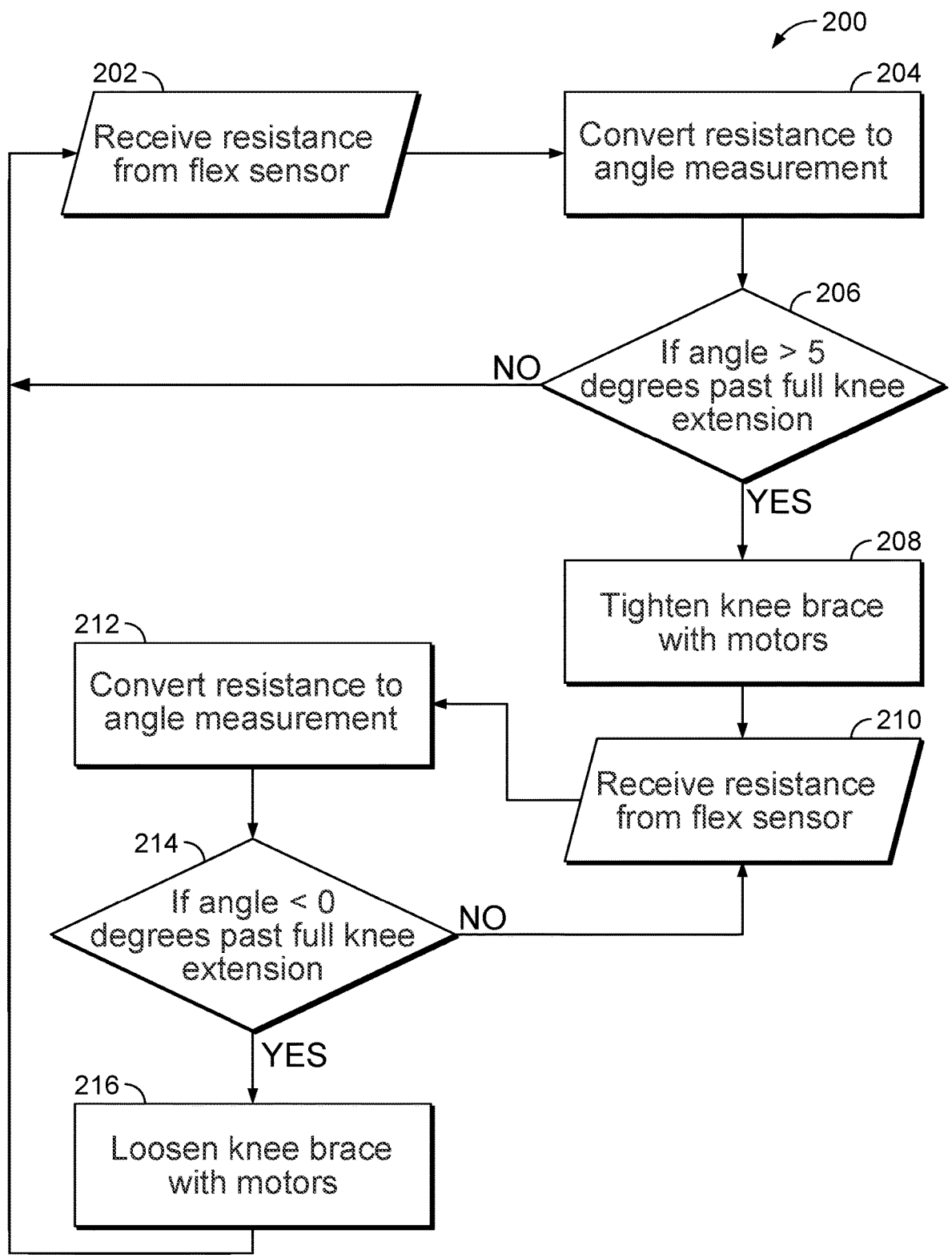
FIG. 13 is a flow diagram of a process of using a knee brace to support a knee.

FIG. 13 is an example of a flow diagram of a process 200 for operating the knee brace 100, 170, or 190. The process 200 includes receiving 202 a signal from a flex sensor indicating a resistance of the flex sensor. For example, the signal from the flex sensor can be received at a controller, such as controller 110 of FIGS. 1A and 1B. The resistance value is converted 204 to an angle measurement. For example, the controller 110 can convert the resistance value to the angle measurement.

A determination 206 is made regarding whether the angle past full knee extension is greater than a first threshold angle, which in this example is 5 degrees. For example, the controller 110 can make the determination of whether the angle past full knee extension is greater than the first threshold angle. If the angle is greater than 5 degrees past full knee extension, the knee brace is tightened by activating 208 one or more motors. For example, the controller 110 can activate the motors 126 and 128. If the angle is not more than 5 degrees past full knee extension, the process 200 returns to step 202 and continues to receive 202 the resistance measurements from the flex sensor. In some examples, other threshold angles can be used. For example, the first threshold angle can be 0°, 1°, 2°, 3°, 4°, 6°, 7°, 8°, 9°, or 10°.

For example, the process 200 can include a calibration step in which the angle measured by the flex sensor when the knee is at full extension is stored as a reference angle in a memory device. At step 206, the measured angle is compared with the reference angle in order to determine the degrees past full knee extension. For example, if the $\theta_{measure}>\theta_{ref}+\theta_{threshold1}$, the knee brace is tightened.

After the knee brace is tightened, the resistance values are continued to be received 210 from the flex sensor. For example, the controller 110 can continue to receive a resistance value from the flex sensor. The resistance value is converted 212 to angle measurement. For example, the controller 110 can convert 212 the resistance value to the angle measurement. A determination is made regarding whether the angle past full knee extension is less than a second threshold angle, which in this example is 0°. For example, the controller 110 can make the determination of whether the angle past full knee extension is less than the second threshold angle. If the angle is less than 0° past full knee extension, the knee brace is loosened 216 by controlling the motors. For example, if $\theta_{measure}<\theta_{ref}+\theta_{threshold2}$, the knee brace is loosened. For example, the controller 110 can control the motors 126, 128 to loosen the knee brace 100. If the angle is equal to or more than the second threshold angle past full knee extension, the process 200 returns to step 210 and continues to receive 210 the resistance measurements from the flex sensor. In some examples, other threshold angles can be used. For example, the second threshold angle can be −1°, 1°, 2°, 3°, or 4°.

In the above example, the first threshold angle and the second threshold angle are different. This gives the user more freedom in the knee movement before the knee brace is tightened. In this example, when the knee is bending up to 5° beyond full knee extension, even though such knee bending may not be normal, the knee brace is not tightened. Once the knee brace is tightened, the knee brace is not loosened until the knee returns to the normal configuration, i.e., the knee does not bend beyond the full knee extension.

The goal of the knee brace 100 is to provide additional support for the knee when the knee is about to become vulnerable by bending in an abnormal degree that may increase the risk of anterior cruciate ligament tear.

In some implementations, the first and second thresholds can be set by the user. For example, the controller 110 can have a user interface, such as a small display and some buttons that allow the user to set the thresholds.

In some implementations, the controller 110 can wirelessly communicate with a computer device, such as a laptop computer or a wearable computer, such as a mobile phone or smart watch, using for example Wi-Fi or Bluetooth. The user can set the first and second thresholds on the computer device and transmit the first and second thresholds to the controller 110.

In some implementations, the knee brace 100 can record knee movements over time, in which the recorded data can be later retrieved and analyzed. For example, during a sports training event, each time the knee brace 100 is triggered to be tightened to provide additional support to the knee, the controller 110 records the time and angle of bending. At the end of the sports training event, the recorded data can be downloaded and analyzed on a computer. For example, if a coach determines that a student athlete bends the knee abnormally a large number of times, the coach can provide extra guidance to the student athlete regarding the correct movements to reduce the risk of anterior cruciate ligament injury. For example, a video may be taken of the sports training event, and the time stamps provided by the controller 110 can help the coach and the athlete identify the video frames that show the athlete bending the knee abnormally. This may help the coach and the athlete identify the circumstances in which the athlete may bend the knee abnormally, and allow the coach and the athlete to develop strategies for preventing abnormal knee bending in the future.

Figure 14:
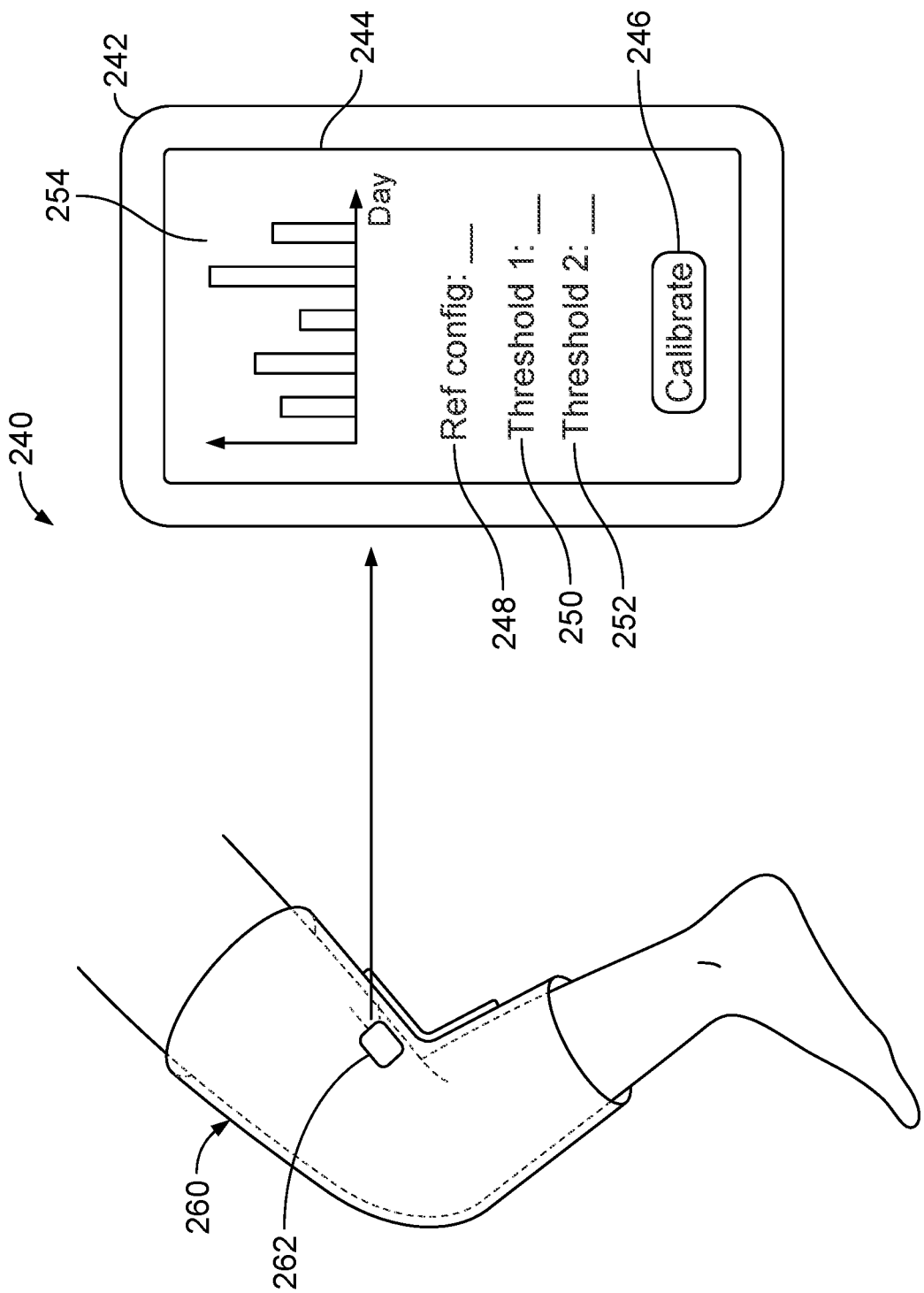
FIG. 14 is a diagram of a system that includes a knee brace and a mobile device.

Referring to FIG. 14, a system 240 includes a knee brace 260 having a controller 262 that is in wireless communication with a mobile device 242, e.g., a mobile smart phone. The mobile device 242 includes a user interface 244 that enables a user to perform various functions. For example, the user interface 244 allows the user to calibrate the knee brace 100 by selecting a "Calibration" button 246. The user interface 244 allows the user to set or view the reference threshold configuration, such as the reference threshold angle, and various threshold values, such as the first threshold angle 250 and the second threshold angle 252. For example, the user interface 244 allows the user to view information 254 derived from measurements of one or more sensors of the knee brace. For example, the information 254 can include statistical information about the number of times that the knee bending angle exceeds a preset value. The user interface 244 can show additional information or be used to configure additional parameters of the knee brace.

Other embodiments are within the scope of the following claims. For example, in some implementations, the sensor 104 can take measurements in two or more degrees of freedom. The sensor 104 can measure not just the bending but also rotation or twisting of the knee. The knee brace 100 can be configured to tighten the flexible sleeve 102 upon detecting that the knee rotates or twists beyond a safety threshold. The knee brace can include two or more sensors to sense the configuration of the flexible sleeve, which indicates the configuration of the knee. The multiple sensors can be calibrated to detect the configuration of the sleeve 102 when the knee is at full extension, and the detected configuration can be stored in a memory device as a reference configuration. Later, the signals from the multiple sensors are used determine a measured configuration of the sleeve 102, and the measured configuration is compared to the reference configuration to estimate whether the knee is at a normal configuration, in which the knee brace 100 continues to stay in a normal state, or whether the knee is at an abnormal configuration, in which the knee brace 100 is tightened to provide additional support to the knee. Other types of sleeve tightening mechanism can also be used.

For example, the controller 110 can control the motors 126 and 128 to apply a variable amount of force to pull the strings 160, 162 to tighten the flexible sleeve 102, and the force can be dependent on the angle of bending of the flexible sleeve. The controller 110 can be configured to control the motors 12\6, 128 to apply a larger force to tighten the flexible sleeve 102 upon detecting that the measured angle of bending is greater than the reference angle of bending, and the greater the difference between the measured angle of bending and the reference angle of bending, the larger the force applied to tighten the flexible sleeve 102.

Various types of sensors can be used to measure the knee bending angle. For example, these sensors can be used: a bidirectional flexible bend sensor available from Flexpoint Sensor Systems, Draper, Utah, a pressure sensor that senses muscle contraction, such as model number SEN-09375 or SEN-09376 from SparkFun Electronics, or a foil strain gauge from RS Pro by Allied. An example of motors that can be used for the knee brace include Onlykxy small mini 1.5-5V DC motors. In some implementations, an infrared sensor or a laser sensor, such as Banner Engineering Q4X laser sensor, can be used to measure the distance between top and bottom of the flexible sleeve 102 to calculate the angle of the knee joint.

In some implementations, the knee brace 100 can be used for rehabilitation. A patient having knee injury may use the knee brace 100 to reduce knee soreness or pain by allowing free knee movements within a predetermined range of motions and preventing knee movements outside of the predetermined range of motions. The knee brace can be in the normal, relaxed state when the knee bending is within the predetermined range of motions, or in the tightened state when the knee bending is outside of the predetermined range of motions. The controller can collect data on the range of motions of the knee that the patient engaged in, and the physical therapist or doctor can use the collected data to improve treatment of the knee injury. For example, the knee brace can be paired with a mobile phone, in which a healthcare app executing on the mobile phone analyzes the collected data. For example, the app can send an alert to the patient and/or the doctor or physical therapist if the app determines that the patient's knee movements may be outside of a prescribed range of movements. For example, the parameters of the knee brace can be adjusted according to the progress of recovery from knee injury. As the user's knee gradually recovers, the range of permitted movements (e.g., of knee bending) also increases.

The knee brace can be useful for preventing other types of injuries or diseases, or for rehabilitation from other types of injuries or diseases, such as posterior cruciate ligament (PCL) injury, medial collateral ligament (MCL) injury, or Osgood-Schlatter disease.

In some implementations, multiple sensors are used to make measurements of various parameters of the knee and/or lower leg, and the combination of measurements are used in determining whether to tighten or relax the sleeve of the knee brace, and how tight the sleeve should be. For example, two flex sensors can be used in which a first flex sensor is positioned at the front of the knee, a second flex sensor is positioned at the back of the knee, and the angle measurements from the first and second sensors are averaged (or weight averaged). Pressure sensors can be attached to the skin of the calf or thigh to measure the contraction of muscle of the calf or thigh. Tension sensors can be used to sense the bending of the knee.

In some implementations, movements of the thigh and lower leg along multiple degrees of freedom are also measured and taken into account when determining whether to tighten or loosen the knee brace. For example, accelerometers are used to sense the movements of the knee joint, thigh, lower leg. This allows the controller to differentiate between, e.g., someone sitting on a chair and stretching the lower leg, or someone running in a soccer match and changing directions in rapid maneuvers.

In some implementations, multiple athletes (e.g., members of a soccer or basketball team) wear the knee braces incorporating the novel features described in this document, and data collected from the knee braces can be used for improving future versions of the knee braces. For example, by analyzing the correlation between knee injuries and the data collected from the knee braces, parameters of the knee brace, such as the first and second threshold angles, can be updated to improve the knee braces in preventing knee injuries. Data collected from athletes practicing various types of sports activities can be used to fine-tune the parameters of the knee braces when used for the sports activities. For example, the first and second threshold angle values may be different for different types of sports activities. For example, the threshold values of knee braces for athletes practicing soccer may be different from the threshold values for of knee braces for athletes practicing figure skating. In some implementations, different specialized knee braces are provided for different types of sports activities, in which each knee brace is specially configured to prevent knee injuries for a particular sport. In some implementations, the knee brace includes a user interface (either directly on the knee brace or through a mobile phone that is paired with the knee brace) that allows the user to select which type of sports activity the user will be engaged in, and the relevant parameters of the knee brace are selected accordingly. This way, the same knee brace can be used for multiple types of sports activities.

In some implementations, artificial intelligence is used to analyze measurements from the sensors of the knee braces worn by multiple users and identify the measurement values that may indicate likelihood of knee injury. For example, the analyses may be used to determine the threshold values for the knee brace when used by users of a certain age group, of a certain gender, of a certain weigh range, when practicing a certain sport activity.

For example, the data collected from the knee braces worn by multiple athletes can be useful to knee injury research. For example, the collected data may be useful in determining whether athletes of certain age groups are more prone to certain knee injuries when practicing certain movements in certain sports activities.

What is claimed is:

1. A knee brace comprising:
   a flexible sleeve that comprises a flexible fabric;
   a memory device configured to store a reference configuration of the flexible sleeve, wherein the reference configuration represents a configuration of the flexible sleeve when a knee of a user is at full extension;
   a first sensor configured to detect a configuration of the flexible sleeve;
   a sleeve tightening mechanism comprising at least one motor and configured to adjust a tightness of the flexible sleeve; and
   a controller configured to receive an output signal representing, or indicative of, the detected configuration from the first sensor, compare the detected configuration with the reference configuration, and control the sleeve tightening mechanism based on a result of a comparison of the detected configuration of the flexible sleeve and the reference configuration of the flexible sleeve;
   wherein the controller is configured to control the sleeve tightening mechanism to tighten the flexible sleeve, as compared to a normal state of the flexible sleeve, upon determining that the flexible sleeve is bent past the reference configuration by a first threshold angle, which indicates that the knee is bent past full extension by the first threshold angle.

2. The knee brace of claim 1 in which the first sensor is configured to measure an angle of bending of the flexible sleeve, and the reference configuration of the flexible sleeve comprises a reference angle of bending of the flexible sleeve.

3. The knee brace of claim 2 in which the controller is configured to compare the measured angle of bending of the flexible sleeve with the reference angle of bending of the flexible sleeve, and control the sleeve tightening mechanism based on a result of a comparison of the measured angle of bending of the flexible sleeve and the reference angle of bending of the flexible sleeve.

4. The knee brace of claim 3 in which the controller is configured to control the sleeve tightening mechanism to tighten the flexible sleeve, as compared to a normal state of the flexible sleeve, if the result of the comparison of the measured angle and the reference angle meets a first criterion.

5. The knee brace of claim 4 in which the controller is configured to control the sleeve tightening mechanism to tighten the flexible sleeve, as compared to the normal state of the flexible sleeve, if the measured angle is greater than the reference angle by a predetermined threshold.

6. The knee brace of claim 2 in which the sleeve tightening mechanism is configured to apply a variable amount of force to tighten the flexible sleeve, and the force is dependent on the measured angle of bending of the flexible sleeve,
   wherein the controller is configured to control the sleeve tightening mechanism to apply a larger force to tighten the flexible sleeve upon detecting that the measured angle of bending is greater than the reference angle of bending, and the greater the difference between the measured angle of bending and the reference angle of bending, the larger the force applied to tighten the flexible sleeve.

7. The knee brace of claim 1 in which the controller is configured to perform a calibration procedure to determine the reference configuration, and store the reference configuration in the memory device.

8. The knee brace of claim 7 in which the controller is configured to perform the calibration procedure to determine a reference angle of bending of the flexible sleeve when the knee brace is worn by a user in a reference position.

9. The knee brace of claim 1 in which the sleeve tightening mechanism comprises at least one string and at least one motor that pulls the at least one string to tighten the flexible sleeve.

10. The knee brace of claim 9 in which the flexible sleeve has a first end and a second end, the flexible sleeve extends from the first end to the second end, the first end forms a first opening, the second end forms a second opening,
wherein the at least one motor comprises at least a first motor and a second motor, the first motor is positioned closer to the first end of the flexible sleeve as compared to the second motor, the second motor is positioned closer to the second end of the flexible sleeve as compared to the first motor, and both the first and second motors are configured to pull the at least one string to tighten the flexible sleeve.

11. The knee brace of claim 1 in which the knee brace is configured to reduce a risk of anterior cruciate ligament tear for a user wearing the knee brace around a knee of the user.

12. The knee brace of claim 1 wherein the flexible sleeve is configured to be worn over the knee of the user, and the controller is configured to tighten the flexible sleeve, as compared to a normal state of the flexible sleeve, upon determining that the flexible sleeve is bent past the reference configuration by the first predetermined threshold angle to provide additional support for the knee to reduce further bending of the knee beyond full extension by more than the first predetermined threshold angle.

13. The knee brace of claim 1 wherein the controller is configured to control the sleeve tightening mechanism to tighten the flexible sleeve upon determining that a backside of the flexible sleeve form an angle greater than 180°.

14. The knee brace of claim 1 wherein the flexible sleeve is configured to be worn over the knee of the user, and the controller is configured to tighten the flexible sleeve, as compared to a normal state of the flexible sleeve, upon analyzing an output signal from the first sensor and determining that knee is bent past full extension by determining that a backside of a thigh above the knee and a backside of a lower leg below the knee form an angle greater than a reference angle.

15. The knee brace of claim 14 wherein the reference angle is 180°.

16. The knee brace of claim 1 wherein the first sensor comprises a flex sensor that is configured to have a resistance that varies in accordance with an amount of bending, and the flex sensor is configured to detect the configuration of the flexible sleeve by measuring the resistance of the flex sensor to detect a bending of the flexible sleeve.

17. The knee brace of claim 16 wherein the flex sensor has a length in a range from 1 inch to 16 inches.

18. The knee brace of claim 1 wherein the first sensor comprises an elongated flex sensor that is attached to the flexible sleeve and extend parallel to a longitudinal direction of the flexible sleeve.

19. The knee brace of claim 18 wherein the knee brace is configured to be worn around the knee and positioned such that the flex sensor is positioned at a backside of the knee and extends from a position above the knee to a position below the knee.

20. The knee brace of claim 19 wherein the knee brace is configured such that, when the knee bends, the flexible sleeve bends along with the knee, and the flex sensor also bends along with the flexible sleeve,
wherein the flex sensor is configured to generate an output that indicates an amount of bending of the flexible sleeve, which in turn indicates an amount of bending of the knee.

21. The knee brace of claim 1 wherein the controller is configured to perform a calibration procedure to determine the reference configuration representing the configuration of the flexible sleeve when the knee is at full extension, and store the reference configuration in the memory device.

22. The knee brace of claim 1 wherein the first predetermined threshold angle is equal to 0°.

23. The knee brace of claim 1 wherein the first predetermined threshold angle is equal to 5°.

24. The knee brace of claim 1 wherein the first predetermined threshold angle is equal to 10°.

25. The knee brace of claim 1 wherein the controller is configured to, after the flexible sleeve has been tightened, receive a second measurement signal from the first sensor, and control the sleeve tightness adjustment mechanism to reduce a tightness of the flexible sleeve in response to determining that a bending angle of the flexible sleeve is either (i) smaller than a reference bending angle, or (ii) larger than a reference bending angle by an amount no greater than a second threshold angle.

26. The knee brace of claim 1 wherein the flexible sleeve comprises an inner sleeve member and an outer sleeve member that wraps around at least a portion of the inner sleeve member, the sleeve tightening mechanism is configured to tighten the outer sleeve member, and the inner sleeve member is configured as a cushion.

27. The knee brace of claim 1 wherein the memory device is configured to store the first threshold angle value and a second threshold angle value;
wherein the knee brace is configured to operate in a first state in which the controller is configured to control the sleeve tightening mechanism to tighten the flexible sleeve, as compared to the normal state of the flexible sleeve, upon determining that the flexible sleeve is bent past the reference configuration by the first threshold angle;
wherein the knee brace is configured to operate in a second state in which the controller is configured to control the sleeve tightening mechanism to tighten the flexible sleeve, as compared to the normal state of the flexible sleeve, upon determining that the flexible sleeve is bent past the reference configuration by the second threshold angle.

28. The knee brace of claim 1, comprising a user interface that allows the user to select which type of sports activity the user will be engaged in, and relevant parameters of the knee brace are selected accordingly.

29. The knee brace of claim 28 wherein the controller is configured to, upon receiving a first user input indicating selection of a first type of sports activity, control the sleeve tightening mechanism to tighten the flexible sleeve, as compared to a normal state of the flexible sleeve, upon determining that the flexible sleeve is bent past the reference configuration by a first threshold angle,
wherein the controller is configured to, upon receiving a second user input indicating selection of a second type of sports activity, control the sleeve tightening mechanism to tighten the flexible sleeve, as compared to a normal state of the flexible sleeve, upon determining that the flexible sleeve is bent past the reference configuration by a second threshold angle different from the first threshold angle.

30. A knee brace comprising:
a flexible sleeve that comprises a flexible fabric;
a memory device configured to store a reference configuration of the flexible sleeve, wherein the reference configuration represents a reference angle of bending of the flexible sleeve;
a first sensor configured to measure an angle of bending of the flexible sleeve;
a sleeve tightening mechanism comprising at least one motor and configured to adjust a tightness of the flexible sleeve; and
a controller configured to receive a first measurement signal from the first sensor representing, or indicative of, the angle of bending ($\theta_{measure}$) of the flexible sleeve, compare the angle of bending of the flexible sleeve with the reference angle of bending ($\theta_{ref}$) of the flexible sleeve, and control the sleeve tightening mechanism to tighten the flexible sleeve, as compared to a normal state of the flexible sleeve, upon determining that the flexible sleeve is bent past the reference angle of bending by a first threshold angle ($\theta_{threshold1}$), $\theta_{measure} > \theta_{ref} + \theta_{threshold1}$;
wherein the controller is configured to continue to control the sleeve tightening mechanism to tighten the flexible sleeve until the controller receives a second measurement signal from the first sensor and determine that the angle of bending ($\theta_{measure}$) of the flexible sleeve beyond the reference angle ($\theta_{ref}$) is less than a second threshold angle ($\theta_{threshold2}$), then the controller is configured to control the sleeve tightening mechanism to reduce the tightening of the flexible sleeve, $\theta_{measure} < \theta_{ref} + \theta_{threshold2}$.

31. The knee brace of claim 30 wherein the second threshold angle is in a range from −1° to 4°.

32. The knee brace of claim 30 wherein the second threshold angle is in a range from −1° to the first threshold angle $\theta_{threshold1}$.

33. A knee brace comprising:
a flexible sleeve that comprises a flexible fabric;
a memory device configured to store a reference configuration of the flexible sleeve;
a first sensor configured to detect a configuration of the flexible sleeve;
a sleeve tightening mechanism configured to adjust a tightness of the flexible sleeve; and
a controller configured to receive an output signal representing, or indicative of, the detected configuration from the first sensor, compare the detected configuration with the reference configuration, and control the sleeve tightening mechanism based on a result of a comparison of the detected configuration of the flexible sleeve and the reference configuration of the flexible sleeve;
wherein the first sensor is configured to measure an angle of bending of the flexible sleeve, and the reference configuration of the flexible sleeve comprises a reference angle of bending of the flexible sleeve;
wherein the sleeve tightening mechanism is configured to apply a variable amount of force to tighten the flexible sleeve, and the force is dependent on the measured angle of bending of the flexible sleeve; and
wherein the controller is configured to control the sleeve tightening mechanism to apply a larger force to tighten the flexible sleeve upon detecting that the measured angle of bending is greater than the reference angle of bending, and the greater the difference between the measured angle of bending and the reference angle of bending, the larger the force applied to tighten the flexible sleeve.

* * * * *